US005230998A

United States Patent [19]

Neurath et al.

[11] Patent Number: 5,230,998

[45] Date of Patent: Jul. 27, 1993

[54] METHOD FOR THE PRESCREENING OF DRUGS TARGETED TO THE V3 HYPERVARIABLE LOOP OF THE HIV-1 ENVELOPE GLYCOPROTEIN GP 120

[76] Inventors: Alexander R. Neurath, 230 E. 79th St., New York, N.Y. 10021; Nathan Strick, 3243 Lawrence Ave., Oceanside, N.Y. 11572; Paul Haberfield, 1666 52nd St., Brooklyn, N.Y. 11204; Shibo Jiang, 316 W. 95th St. Apr. 525, New York, N.Y. 10025

[21] Appl. No.: 735,640

[22] Filed: Jul. 25, 1991

[51] Int. Cl.$^5$ .......................................... G01N 33/545

[52] U.S. Cl. .................................. 435/7.1; 435/7.72; 435/7.9; 435/7.92; 435/7.94; 435/7.95; 435/974; 436/532

[58] Field of Search .................... 435/5, 7.1, 7.2, 7.92; 530/328

[56] References Cited

FOREIGN PATENT DOCUMENTS

WO89/11277 11/1989 PCT Int'l Appl. .

OTHER PUBLICATIONS

Durda et al.: "Murine Mab . . . Blocking Activities" Int. Conf. AIDS p. 537, #Th.CO.26 Jun. 8, 1989.
Schols et al.: "Dextran Sulfate . . . Infected with HIV-1" Virology, 175, pp. 556-561 (1990).
De Clerca: "Basic Approaches to Anti-Retroviral Treatment" J of AIDS vol. 4, No. 3.
Tifssen: Laboratory Techniques in Biochemistry & Molecular Biology 1985 pp. 9-20.
Kawamura: Immunofluorescence in Medical Science 1983 pp. 9-11.
A. Robert Neurath et al, Journal of General Virology (1990) 71 pp. 85-95.
A. R. Neurath et al, Molecular Immunology, vol. 27, No. 6, 1990, pp. 539-549.
Masanori Baba et al, Biochemical and Biophysical Research Communications, vol. 155, No. 3, 1988, pp. 1404-1411.
Michael A. Skinner et al, AIDS Research and Human Retroviruses, vol. 4, No. 3, 1988 pp. 187-197.
James R. Rusche et al, Proc. Natl. Acad. Sci USA, vol. 85, pp. 3198-3202, May 1988. Medical Sciences.
Thomas P. Palker et al, Proc. Natl. Acad. Sci. USA, vol. 85, pp. 1932-1936, Mar. 1988.
Susanne Modrow et al, Journal of Virology, Feb. 1987, pp. 570-578.
Gregory J. LaRosa et al, Science, vol. 249, Aug. 24, 1990, pp. 932-935.
Kashi Javaherian et al, Science, vol. 250, Dec. 1990, pp. 1590-1593.
Kashi Javaherian et al, Proc. Natl. Acad. Sci. USA, vol. 86, pp. 6768-6772, Sep. 1989.
Toshio Hattori, FEBS Letters, vol. 248, No. 1,2, May 1989 pp. 48-52.
Shinji Harada, Science, vol. 229, pp. 563-566, Aug. 1985.
J. L. Matthews et al, Transfusion, vol. 28, No. 1-1988, pp. 81-83.
J. Goudsmit et al, Proc. Natl. Acad. Sci. USA. vol. 85, pp. 4478-4482, Jun. 1988.
Marc Girard et al, Proc. Natl. Acad. Sci. USA. vol. 88, pp. 542-546, Jan. 1991.
Richard D. Levere et al, Proc. Natl. Acad. Sci. USA, vol. 88, pp. 1756-1759, Mar. 1991.
Mark Cushman et al, J. Med. Chem. 1991, 34, 329-337.
Jan Balzarini et al, Biochemical and Biophysical Research Communications, vol. 136, No. 1, Apr. 1986, pp. 64-71.
Lawrence N. Callahan, Journal of Virology, Mar. 1991, pp. 1543-1550, 1991.
Erik DeClercq, Journal of Acquired Immune Deficiency Syndromès, vol. 4, No. 3, 1991, pp. 207-218.
Mark Cushman et al, Journal of Medicinal Chemistry, 1991, vol. 34, No. 1, pp. 337-342.
D. Schols et al, Virology, 175, 556-561 (1990).
R. G. Gonzalez et al, Biochimica et Biophysica Acta, 562 (1979) pp. 534-545.
D. Schols et al, Proc. Natl. Acad. Sci. USA, vol. 86, pp. 3322-3326, May 1989.
James L. Weaver et al, AIDS Research and Human Retroviruses, vol. 6, No. 9, 1990 pp. 1125-1130.
A. R. Neurath et al, Vaccines 91, 1991, pp. 15-21.

*Primary Examiner*—Christine M. Nucker
*Assistant Examiner*—Jeffrey Stucker
*Attorney, Agent, or Firm*—Frishauf, Holtz, Goodman & Woodward

[57] ABSTRACT

A method for the rapid screening of a drug targeted to the V3 hypervariable loop of the human immunodeficiency virus type 1 or type 2 envelope glycoprotein gp 120 comprising measuring the inhibitory effect of the drug on the interaction between gp 120 (or an antigen comprising the V3 hypervariable loop of HIV 1 gp 120 or HIV 2 gp 120) and antibodies specific for the V3 hypervariable loop, and anti-HIV chemotherapy with drugs binding to the V3 hypervariable loop.

7 Claims, 13 Drawing Sheets

METHOD FOR THE PRESCREENING OF DRUGS TARGETED TO THE V3 HYPERVARIABLE LOOP OF THE HIV-1 ENVELOPE GLYCOPROTEIN GP 120

GOVERNMENT RIGHTS

This invention was made with United States government support under Grant CA 43315 from the NIH. The United Stated government have certain rights in this invention.

BACKGROUND OF THE INVENTION

1. Field of the Invention

The present invention concerns: (a) methods for the rapid screening of drugs targeted to the V3 hypervariable loop of the human immunodeficiency virus type 1 (HIV-1) or type 2 (HIV-2) envelope glycoproteins and (b) the use of these drugs for chemotherapy and prophylaxis of HIV-1 (or HIV-2) infections and the acquired immunodeficiency syndrome (AIDS).

2. Background Information

Antiviral drugs considered for therapy of Lentivirus infections can be classified according to: (1) the virus or cellular components they are targeted to (envelope glycoproteins and other structural components of the virion, virally-encoded enzymes, viral genes or their transcripts or specific cellular factors essential for virus replication) or (2) temporal stages in the virus replicative cycle, starting with attachment of the virus to cells, fusion with target cell membranes and virus uncoating (Mitsuya, H., Yarchoan, R., and Broder, S. (1990), "Molecular Targets for AIDS Therapy", *Science,* 249, 1533–1544; De Clercq, E. (1991), "Basic Approaches to Anti-retroviral Treatment", *J. AIDS,* 4, 207–218).

Drugs targeted to early steps in virus replication may have potential not only for immunotherapy of ongoing infections but also for prophylaxis, and thus may complement efforts to develop antiviral vaccines. Aurintricarboxylic acid (ATA), known as a potent inhibitor of protein-nucleic acid interactions (Gonzalez, R. G., Blackburn, B. J., Schleich, T. (1979), "Fractionation and Structural Elucidation of the Active Components of Aurintricarboxylic Acid, a Potent Inhibitor of Protein Nucleic Acid Interactions", *Biochem. Biophys. Acta,* 562, 534–545), was shown to inhibit the cytopathogenicity and replication of the human immunodeficiency virus type 1 (HIV-1) as measured by the production of the nucleocapsid protein P24 (Balzarini, J., Mitsuya, H., De Clercq E., Broder, S. (1986), "Aurintricarboxylic Acid and Evans Blue Represent Two Different Classes of Anionic Compounds Which Selectively Inhibit the Cytopathogenicity of Human T-cell Lymphotropic Virus Type III/Lymphadenopathy-associated Virus", *Biochem. Biophys. Res. Comm.,* 136, 64–71).

Originally thought to inhibit HIV-1 replication by acting on the virus reverse transcriptase, it was concluded from subsequent studies that ATA also exerts its antiviral effects by attaching to the HIV-1 envelope glycoprotein gp120, thus inhibiting the interaction between HIV-1 virions and cellular CD4 receptors (Schols, D., Baba M., Pauwels, R., Desmyter, J., and De Clercq, E. (1989), "Specific Interaction of Aurintricarboxylic Acid With the Human Immunodeficiency Virus/CD4 Cell Receptor", *Proc. Natl. Acad. Sci. USA.* 86, 3322–3326; Cushman, M., Wang P., Chang, S. H., Wild, C., De Clercq, E., Schols, D., Goldman, M. E., and Bowen, J. A. (1991), "Preparation and anti-HIV Activities of Aurintricarboxylic Acid Fractions and Analogues: Direct Correlation of Antiviral Potency with Molecular Weight", *J. Med. Chem.,* 34, 329–337).

It was reported several years ago that ATA inhibited the replication of HIV-1 in vitro (Balzarini et al., (1986), *Biochem. Biohys. Res. Comm.,* 136, 64–71). Similar effects were observed with other polyanionic compounds having several benzene rings in their structure (Evans blue, suramine and fuchsin; Balzarini et al., (1986) supra; Baba, M., Schols, D., Pauwels, R., Balzarini, J., De Clercq, E., (1988), "Fuchsin Acid Selectively Inhibits Human Immunodeficiency Virus (HIV) Replication in vitro", *Biochem. Biophys. Res. Commun.,* 155, 1404–1411). These compounds inhibited the reverse transcriptase of HIV-1, a possible mechanism for explaining their antiviral effect. This conclusion appears to be in agreement with the well established inhibitory effect of ATA on interactions between proteins and nucleic acids (Gonzalez et al, (1979), *Biochem. Biophys. Acta,* 562, 534–545). Commercially available ATA is prepared by treatment of salicylic acid with formaldehyde in the presence of sulfuric acid and sodium nitrite. The resulting product is a heterogeneous mixture containing monomeric ATA and a series of ATA polymers (Gonzalez et al., (1979), supra., Cushman et al., (1979), *J. Med. Chem.,* 34, 329–337).

A direct correlation between the molecular mass of ATA polymers and their inhibitory effect on HIV-1 reverse transcriptase and on antiviral activity was established (Cushman et al., (1991); *J. Med. Chem.,* 34, 329–337). The inhibitory activity of ATA on HIV-1 reverse transcriptase could be explained by binding of ATA (ATA polymers) to the enzyme protein.

Results of additional studies demonstrated that reverse transcriptase is not the only target for ATA. It was shown that ATA as well as Evans blue inhibited the interaction of the CD4 receptor for HIV-1, expressed on the surface of cells, with gp120 or with anti-CD4 monoclonal antibodies (Schols et al., (1989), *Proc. Natl. Acad. Sci. USA,* 86, 3322–3326; Schols et al, (1990), *Virology,* 175, 556–561; Weaver, J. L., Gergely, P., Pine, P. S., Patzer, E., Aszalos, A. (1990), "Polyionic Compounds Selectively Alter Availability of CD4 Receptors for HIV Coat Protein rgp120, *AIDS Res. & Hum. Retro.,* 6, 1125–1130).

However, ATA is an inefficient inhibitor of the reaction between recombinant gp120 and recombinant CD4, and complete inhibition of this reaction can be observed only at high concentrations of ATA (≈1 mg/ml).

Several polyanionic substances (dextran sulfate, pentosan polysulfate, heparin, Evans blue, suramin and ATA) were also reported to inhibit the reaction of gp120 expressed on the surface of HIV-1-infected cells with monoclonal anti-gp120 antibodies (Schols et al., (1990), *Virology,* 175, 556–561; De Clercq, (1991), *J. AIDS.* 4, 207–218). These results suggest the occurrence of multiple target sites for ATA and for other polyanionic compounds on HIV-1 proteins. The availability of a multitude of antibodies with predetermined specificity, generated by immunization with synthetic peptides derived from the entire sequence of HIV-1 gp120/gp41, as reported in (Neurath et al., (1990), *Molec. Immunol.,* 27, 539–549; Neurath and Strick, (1990), J. Gen. Virol., 71, 85–95) offers the possibility to delineate precisely the target site(s) for ATA on HIV-1 gp120.

The gp120 V3 hypervariable loop is discussed in the following publications: Goudsmit, J. (1988), "Immunodominant B-cell Epitopes of the HIV-1 Envelope Recognized by Infected and Immunized Hosts," *AIDS*, 2, S41–S45; Goudsmit, J., Debouck, C., Meloen, R. H., Smit, L., Bakker, M., Asher, D. M., Wolff, A. V., Gibbs Jr., C. J., and Gajdusek, D. C. (1988), "Human Immunodeficiency Type 1 Neutralization Epitope with Conserved Architecture Elicits Early Type-specific Antibodies in Experimentally Infected Chimpanzees", *Proc. Natl. Acad. Sci. USA*, 85, 4478–4482; Goudsmit, J., Kuiken, C. L., and Nara, P. L. (1989), "Linear Versus Conformational Variation of V3 Neutralization Domains of HIV-1 During Experimental and Natural Infection", *AIDS*, 3, S119–S123; Linsley, P. S., Ledbetter, J. A. , Kinney-Thomas, E., and Hu, S. L. (1988), "Effects of Anti-gp120 Monoclonal Antibodies on CD4 Receptor Binding by the env Protein of Human Immunodeficiency Virus Type 1", *J. Virol.*, 62, 3695–3702; Matsushita, S., Robert-Guroff, M., Rusche, J., Koito A., Hattori, T., Hoshino, H., Javaherian, K., Takatsuki, K., and Putney, S. D. (1988), "Characterization of a Human Immunodeficiency Virus Neutralizing Monoclonal Antibody and Mapping of the Neutralizing Epitope", *J. Virol.*, 62, 2107–2114; Palker, T. J., Clark, M. E., Langlois, A. J., Matthews, T. J., Weinhold, K. J., Randall, R. R., Bolognesi, D. P. and Haynes, B. F. (1988), "Type-Specific Neutralization of the Human Immunodeficiency Virus with Antibodies to env-encoded Synthetic Peptides", *Proc. Natl. Acad. Sci. USA*, 85, 1932–1936; Rusche, J. R., Javaherian, K., McDanal, C., Petro, J., Lynn, D. L., Grimaila, R., Langlois, A., Galo, R. C., Arthur, L. O., Fischinger, P. J., Bolognesi, D. P., Putney, S. D. and Matthews, T. J. (1988), "Antibodies that Inhibit Fusion of Human Immunodeficiency Virus-infected Cells Bind a 24-amino Acid Sequence of the Viral Envelope, gp120", *Proc. Natl. Acad. Sci. USA*, 85, 3198–3202; Skinner, M. A., Langlois, A. J., McDanal, C. B., McDougal, J. S., Bolognesi, D. P., and Matthews, T. J. (1988), "Neutralizing Antibodies to an Immunodominant Envelope Sequence do not Prevent gp120 Binding to CD4", *J. Virol.*, 62, 4195–4200; Kenealy, W. R., Matthews, T. J., Ganfield, M. C., Langlois, A. J., Waselefsky, D. M., and Petteway, Jr. S. R. (1989), "Antibodies from Human Immunodeficiency Virus-infected Individuals Bind to a Short Amino Acid Sequence that Elicits Neutralizing Antibodies in Animals," *AIDS Res. Human Retroviruses*, 5, 173–182; Javaherian, K., Langlois, A. J., McDanal, C., Ross, K. L., Eckler, L. I., Jellis, C. L., Profy, A. T., Rusche, J. R., Bolognesi, D. P., Putney, S. D., and Matthews, T. J. (1989), "Principal Neutralizing Domain of the Human Immunodeficiency Virus type 1 Envelope Protein, *Proc. Natl. Acad. Sci. USA*, 86, 6768–6772; Javaherian, K., Langlois, A. J., LaRosa, G. J., Profy, A. T., Bolognesi, D. P., Herlihy, W. C., Putney, S. C., Matthews, T. J. (1990), "Broadly Neutralizing Antibodies Elicited by the Hypervariable Neutralizing Determinant of HIV-1", *Science*, 250, 1590–1593; Fung, M. S. C., Sun, C. R. Y., Liou, R. S., Gordon, W.; Chang, N. T., Chang, T. W., and Sun, N. C. (1990), "Monoclonal Anti-idiotypic Antibody Mimicking the Principal Neutralization Site in HIV-1 gp120 Induces HIV-1 Neutralizing Antibodies in Rabbits" *J. Immunol.*, 145, 2199–2206; Hart, M. K., Palker, T. J. Matthews, T. J., Langlois, A. J., Lerche N. W., Martin, M. E. Scearce, R. M., McDanal, C., Bolognesi, D. P., and Haynes, B. F. (1990), "Synthetic Peptides Containing T and B Cell Epitopes From Human Immunodeficiency Virus Envelope gp120 Induce anti-HIV Proliferative Responses and High Titers of Neutralizing Antibodies in Rhesus Monkeys., *J. Immunol.*, 145, 2677–2685; Neurath et al, (1990), *J. Gen. Virol.*, 71, 85–95; Profy, A. T., Salinas, P. A., Eckler, L. I., Dunlop, N. M., Nara, P. L., and Putney, S. C., (1990), "Epitopes Recognized by the Neutralizing Antibodies of an HIV-1-infected Individual", *J. Immunol.*, 144, 4641–4647 and Scott, Jr., C. F., Silver, S., Profy, A. T., Putney, S. D., Langlois A., Weinhold, K., and Robinson, J. E. (1990), "Human Monoclonal Antibody that Recognizes the V3 Region of Human Immunodeficiency Virus gp120 and Neutralizes the Human T-Lymphotropic Virus type $III_{MN}$ Strain," *Proc. Natl. Acad. Sci. USA*. 87, 8597–8601.

PCT WO 89/11277 discusses compositions for the inhibition of replication of human immunodeficiency virus, containing one or more porphyrins possessing antiviral activity.

SUMMARY OF THE INVENTION

It is an object of the invention to provide methods for the rapid screening (prescreening) of drugs targeted to the V3 hypervariable loop of the human immunodeficiency virus (HIV) type 1 or type 2 envelope glycoproteins.

It is another object of the invention to provide methods for treating a patient infected with HIV-1 or HIV-2, including treatment of AIDS, or preventing HIV-1 or HIV-2 infection.

It is a further object of the invention to provide methods for immunotherapy of HIV-1 o HIV-2 infections by providing antibodies to the aforementioned drugs in combination with or subsequent to administration of the drugs.

The above objects, as well as other objects, aims and advantages are satisfied by the present invention.

The present invention concerns a method for the rapid screening of a drug targeted to the V3 hypervariable loop of the human immunodeficiency virus type 1 or type 2 envelope glycoprotein gp 120 comprising measuring the inhibitory effect of the drug on the interaction between gp 120 (or an antigen comprising the V3 hypervariable loop of HIV-1 gp120 or HIV-2 gp120) and antibodies (polyclonal or monoclonal) specific for the V3 hypervariable loop of HIV-1 gp 120 or HIV-2 gp 120. The antigen comprising the V3 hypervariable loop of gp 120 can be a peptide corresponding to the V3 hypervariable loop of gp 120 (34 to 40 amino acids for HIV-1 gp 120 depending on the antigenic subtype) or the entire sequence of HIV-1 gp 120 (approximately 518 amino acids).

A method for the rapid screening of a drug targeted to the V3 hypervariable loop of the human immunodeficiency virus type 1 or type 2 envelope glycoprotein gp 120 according to the invention comprises (a) incubating
  (i) a first antibody, the first antibody capable of binding to the V3 hypervariable loop of HIV-1 9p 120 or HIV-2 gp 120,
  (ii) a drug to be screened and
  (iii) an antigen comprising the V3 hypervariable loop of HIV-1 gp 120 or HIV-2 gp 120,
(b) washing and removing excess unbound first antibody,
(c) detecting the bound antibody to the V3 hypervariable loop of HIV-1 gp 120 or HIV-2 gp 120 by (i) adding a labeled second antibody, the second antibody being capable of binding with the first antibody, (ii) washing and removing excess unbound second antibody, and (iii) determining the amount of the label, (d) repeating steps (a) to (c) in the absence of the drug, and (e) determining the inhibitory effect of the drug, in percentages, by the following formula:

$$\frac{\text{(quantity of the label in the absence of the drug)} - \text{(quantity of the label in the presence of the drug)}}{\text{quantity of the label in the absence of the drug}} \times 100.$$

Another method for the rapid screening of a drug targeted to the V3 hypervariable loop of the human immunodeficiency virus type 1 or type 2 envelope glycoprotein gp 120 comprises (a) incubating (i) a labeled antibody which is capable of binding to the V3 hypervariable loop of HIV-1 gp 120 or HIV-2 gp 120, (ii) a drug to be screened and (iii) an antigen comprising the V3 hypervariable loop of HIV-1 gp 120 or HIV-2 gp 120, (b) washing and removing excess unbound labeled antibody, (c) determining the amount of the label, (d) repeating steps (a) to (c) in the absence of the drug and (e) determining the inhibitory effect of the drug, in percentage, by the following formula:

$$\frac{\text{(quantity of the label in the absence of the drug)} - \text{(quality of the label in the presence of the drug)}}{\text{quantity of the label in the absence of the drug}} \times 100.$$

A further method for the rapid screening of a drug targeted to the V3 hypervariable loop of the human immunodeficiency virus type 1 or type 2 envelope glycoprotein gp 120 comprises (a) incubating (i) an antibody, the antibody being capable of binding to the V3 hypervariable loop of HIV-1 gp 120 or HIV-2 gp 120, (ii) a drug to be screened and (iii) a labeled antigen, the antigen comprising the V3 hypervariable loop of HIV-1 gp 120 or HIV-2 gp 120, (b) washing and removing excess unbound labeled antigen, (c) determining the amount of the label, (d) repeating steps (a) to (c) in the absence of the drug and (e) determining the inhibitory effect of the drug, in percentage, by the following formula:

$$\frac{\text{(quantity of the label in the absence of the drug)} - \text{(quantity of the label in the presence of the drug)}}{\text{quantity of the label in the absence of the drug}} \times 100.$$

The present invention is also directed to a method for screening and selecting anti-viral drugs directed to regions other than to the V3 hypervariable loop of HIV-1 gp 120 or HIV-2 gp 120 and to virus proteins other than those of HIV-1 or HIV-2. Accordingly, the present invention is directed to a method for screening and selecting antiviral drugs based on their mode of action. The method comprises measuring the inhibitory effect of a drug on the interaction between a functionally important site on a viral protein, e.g., an epitope, and an antibody (polyclonal or monoclonal antibody) directed against the functionally important site. An effective drug in such screening method is one that inhibits the binding of the antibody to the functionally important site of the viral protein. It is expected that a drug which inhibits the aforesaid binding will be an effective antiviral drug. Accordingly, all the aforementioned methods for the screening of a drug targeted to the V3 hypervariable loop of the human immunodeficiency virus type 1 or type 2 envelope glycoprotein gp 120 would be applicable to the screening of a drug targeted to a viral protein other than HIV-1 gp 120 or HIV-2 gp 120.

The present invention is further directed to a method for treating or preventing HIV-1 (or HIV-2) infection of humans comprising administering to a patient a pharmaceutically effective anti HIV-1 (or anti-HIV-2) amount of at least one compound (drug) or a salt thereof, either alone, or in admixture with a carrier, the compound (drug) being capable of binding to the gp 120 V3 hypervariable loop of HIV-1 (or HIV-2) and thereby inhibiting or inactivating the biological function of the V3 hypervariable loop of HIV gp 120.

Another method for treating or preventing HIV-1 (or HIV-2) according to the invention comprises the aforementioned method in conjunction with the further administration to the patient of a second anti-HIV-1 (or anti-HIV-2) compound (drug) in a pharmaceutically effective anti-HIV-1 (or anti HIV-2) amount, or salt thereof, either alone or in admixture with a carrier. The second compound (drug) targeted to a gp 120 region other than the V3 hypervariable loop of HIV-1 (or HIV-2) gp 120. The second drug can be targeted to, for example, reverse transcriptase, HIV-1 (or HIV-2) protease or HIV-1 (or HIV-2) ribonuclease H.

The present invention thus also concerns method for treating or preventing HIV-1 or HIV-2 infection comprising administering to a patient a pharmaceutically effective anti-HIV-1 or anti-HIV-2 amount of at least one compound or a salt thereof, either alone, or in admixture with a carrier, the compound being capable of binding to the gp 120 V3 hypervariable loop of HIV-1 or HIV-2 and thereby inhibiting the biological function of the V3 hypervariable loop, and which further comprises administering to the patient a second anti-HIV-1 or anti HIV-2 compound in a pharmaceutically effective anti-HIV 1 or anti HIV-2 amount or a salt thereof, either alone or in admixture with a carrier, the second compound being targeted to a gp 120 region other than to the V3 hypervariable loop.

The present invention also relates to an immunotherapy method against HIV-1 (or HIV-2) infection by administering to a human patient an effective anti-HIV-1 (or anti-HIV 2 amount) of an anti-HIV-1 (or anti-HIV-2) drug and then administering to the patient antibodies (polyclonal or monoclonal) directed against the drug. The administration of such antibodies to the patient can be carried out, for example, by intramuscular or intravenous administration.

BRIEF DESCRIPTION OF THE DRAWINGS

FIG. 4 comprises bar graphs depicting the interaction of aurintricarboxylic acid (ATA) with full length V3 hypervariable loop peptides from gp120 of distinct HIV-1 isolates (clones).

DETAILED DESCRIPTION OF THE INVENTION

Figure 1D:
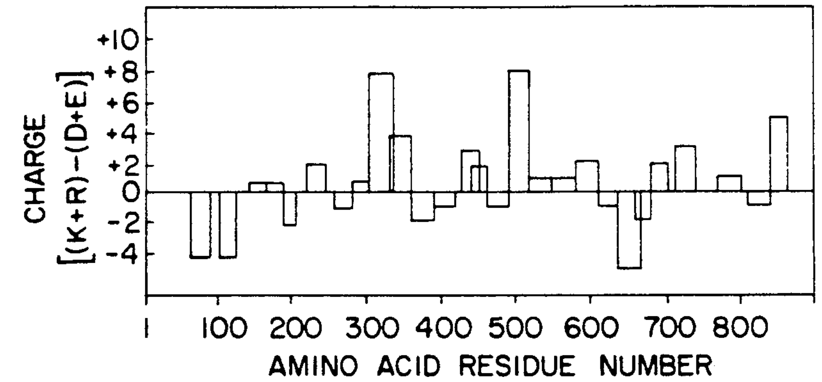
FIG. 1 comprises four bar graphs concerning the interaction of aurintricarboxylic acid (ATA) with the V3 hypervariable loop of gp120 and with distinct peptides derived from the sequence of gp160.
FIG. 1A: Inhibitory effect of ATA (50 μg/ml) on the reaction of antibodies to peptides from the sequence of HIV-1 gp160 with gp120 or gp160. gp120-coated wells were used for antisera to peptides from gp120 and gp160-coated wells were used with antisera to peptides from gp41.
FIG. 1B: Inhibitory effect of ATA (50 μg/ml) on the reaction between antibodies to peptides from gp120/gp41 and homologous peptides.
FIG. 1C: binding of ATA to wells coated with distinct peptides from the sequence of gp160, as determined by subsequent binding of anti-ATA antibodies. FIG. ID: Net electric charge of peptides from the sequence of gp160, determined by subtracting the number of aspartic (D) and glutamic (E) residues from the sum of lysine (K) and arginine (R) residues present in distinct segments of the gp160 sequence. The horizontal dotted line indicates the boundary between non-significant and significant inhibition, established from three times repeated experiments.

The results reported here indicate that the primary attachment site for ATA on gp120 is the V3 hypervariable loop. A monoclonal antibody (NEA 9284), whose adsorption to cell-associated gp120 was reported to be inhibited by polyanionic substances (Schols et al., (1990), *Virology*, 175, 556-561) was also found to be specific for the V3 hypervariable loop. This was established by epitope mapping using peptides from gp120. However unlike ATA, other polyanionic substances reported to inhibit HIV-1 replication in vitro (Evans blue, fuchsin and dextran sulfate), as well as many other polyanionic substances for which data concerning their anti-HIV-1 antiviral effects are not available, did not react with the V3 hypervariable loop as determined by RIA (ELISA) tests (Table 1, hereinbelow).

The inhibitory effect of ATA on gp120-antibody interactions was observed in the presence of an excess of serum proteins used in the medium for these tests. It has been reported recently that the binding of gp120 to monoclonal antibodies specific for the V3 hypervariable loop was blocked in the presence of a 20-fold excess of dextran sulfate over gp120 in the absence of other proteins (Callahan, L., Phelan, M., Mallinson M., and Norcross, M. A. (1991), "Dextran Sulfate Blocks Antibody Binding to the Principal Neutralizing Domain of Human Immunodeficiency Virus Type 1 Without Interfering with gp120-CD4 Interactions", *J. Virol.*, 65, 1543-1550). The inhibitory effect of dextran sulfate on gp120-antibody binding under these conditions was confirmed. The apparently contradictory results concerning binding of dextran sulfate to gp120 obtained by different methods can probably be explained by differences in equilibrium constants defining the binding reaction of gp120 with ATA and dextran sulfate, respectively. In this respect, it is noted that ATA remained bound to gp120 after removal of the excess of the compound, as demonstrated by subsequent binding to gp120 of anti-ATA antibodies. The relatively weak binding of dextran sulfate to the V3 hypervariable loop may contribute to the ineffectiveness of this substance in inhibiting HIV-1 replication in vivo (Mitsuya et al., (1990), *Science*, 249, 1533-1544).

The multiple targets on HIV-1 proteins for ATA, a mixture of monomers and different sized polymers, does not allow a precise explanation for its antiviral effects. However, it was recognized that the targets for monomeric and polymeric ATA were distinct (Cushman et al., (1991), *J. Med. Chem.*, 34, 329-337; Cushman, M., Kanamathareddy, S., De Clercq, E., Goldman, M. E., Bowen, J. A. (1991), "Synthesis and Anti-HIV Activities of Low Molecular Weight Aurintricarboxylic Acid Fragments and Related Compounds," J. Med. Chem., 34, 337-342).

The results presented herein suggest that the primary target for monomeric ATA is the V3 hypervariable loop of HIV-1 gp120. This segment of the virus envelope glycoprotein encompasses the principal neutralizing determinant and was reported to be involved in the process of virion-cell membrane fusion (Rusche et al., (1988); *Proc. Natl. Acad. Sci. USA.* 85, 3198-3202); Kido, H., Fukotomi A., and Katunuma N. (1990), "A Novel Membrane-bound Serine Esterase in Human T4+Lymphocytes Immunologically Reactive With Antibody Inhibiting Syncytia Induced by HIV-1", *J. Biol. Chem.*, 265, 21979-21985).

It is considered that because of the biologically important role of the V3 loop in the life cycle of HIV-1, substances targeted to this segment of the virus envelope were effective in preventing virus replication. The immunological methods described herein which are designed to search for potential antiviral drugs with such properties are expected to enhance progress in chemotherapy, and in prophylaxis, of HIV-1 infections.

Compounds with antiviral activity belonged to several categories of substances (Table 1 hereinafter). Thus, anionic nature does not represent a requirement necessary for interaction of these compounds with the positively charged V3 hypervariable loop of gp120.

The amino acid sequence variability of the V3 hypervariable loops may result in differences in binding patterns for distinct compounds, as suggested by the results shown in FIG. 4. The probable common functional role of V3 hypervariable loops independent of sequence variability (LaRosa, G. J., Davide, J. P., Weinhold, K., Waterbury, J. A., Profy, A. T., Lewis, J. A., Langlois, A. J., Dreesman, G. R., Boswell, R. N., Shadduck, P., Holley, L. H., Karplus, M., Bolognesi, D. P., Matthews, T. J., Emini, E. A., and Putney, S. D. (1990), "Conserved Sequence and Structural Elements in the HIV-1 Principal Neutralizing Determinant", *Science*, 249, 932-935) raises the possibility that a selected single chemical will bind to V3 loops of most HIV-I isolates and may thus become universally useful as a chemotherapeutic agent against HIV-I infections. The observed binding of ATA to synthetic peptides representing V3 loops of several HIV-1 isolates (clones) (FIG. 4), in contrast with the restricted immunological cross-reactivity between these peptides (Neurath and Strick, (1990), *Molec. Immunol.* 27, 539-549), supports this possibility.

The results reported herein demonstrate that ATA is an effective inhibitor of HIV-1 replication as reflected by analysis of two markers of HIV infection, viral antigen (P24) and viral DNA. Viral DNA was almost undetectable in ATA-treated cultures. The lack of toxicity of the drug, at the concentrations used, for H9, U937 and MT-2 cells, make it an attractive candidate for use in humans. The combined effects of AZT and ATA, and other compounds shown to be effective in Table 1, hereinbelow, against HIV-1 are also contemplated by the present invention, since synergistic drug combinations would offer means for alleviating toxicity due to AZT, observed in clinical settings. Contemplated combinations include, for example, AZT+ATA, AZT+-chlorin $e_6$; AZT+deuteroporphyrin IX, 2,4(4,2) hydroxyethyvinyl; and AZT+meso-tetra(4-carboxyphenyl)porphine.

Diagnostics

The antibodies for use in immunoassays in the present invention can be polyclonal antibodies or monoclonal antibodies.

A monoclonal antibody can be prepared according to known methods, for example, by the procedures of immunization, cell fusion, screening, and cloning, using the procedures of G. Kohler and C. Milstein (1975), *Nature* (Lond.), 256, 495.

In selection of the animal to be immunized for production of a monoclonal antibody, the animal species and the immune response to the antigen are important. Generally speaking, stable antibody-producing hybridomas will be frequently formed with good efficiency when the spleen cells to be used and myeloma are of the same animal species. Particularly preferred is the use of BALB/c mice. Preferred myeloma cell species include P3·X63·Ag8(X63), P3·NS−1/1·Ag4·1(NS−1), SP2/O·Ag14(SP−2) and FO.

The antibody or antigen in the immunoassays of the invention may be immobilized to a support.

Known immobilization techniques and materials can be employed. Examples of immobilization methods include the physical adsorption method, the ion bonding method, the covalent bonding method, the support crosslinking method, the supportless crosslinking method and the inclusion method.

The support may be one generally used, and the choice is not particularly limited. Selection of the support depends on the properties of the material to be immobilized, but it is also necessary to consider the size of particles, the surface area in the three-dimensional network structure, the ratio of hydrophilic sites to hydrophobic sites, chemical composition, strength to pressure, etc. of the support. Typical examples of the support include polystyrene, polysaccharide derivatives such as cellulose, dextran, or agarose; synthetic polymers such as polyacrylamide gel, or polystyrene resin; and inorganic materials such as porous glass, or metal oxide.

With the physical adsorption method, where the material is immobilized by physical adsorption onto a water-insoluble support, examples of particularly preferred supports include polystyrene, inorganic substances such as activated charcoal, porous glass, acidic white clay, bleached clay, kaolinite, alumina, silica gel, bentonite, hydroxyapatite, calcium phosphate, metal oxide, or ceramic; a natural polymer such as starch or gluten; or a porous synthetic resin. Adsorption hydrophobically onto a support having hydrophobic groups such as butyl- or hexyl-"SEPHADEX" (as used herein, the trademark "SEPHADEX" refers to a dry, insoluble powder composed of macroscopic beads which are synthetic, organic compounds derived from polysaccharide dextran) is also possible.

With the ion bonding method, where the material is immobilized by binding ionically to a water-insoluble support having ion exchange groups, particularly preferred examples of the support include polysaccharides having ion exchange groups such as DEAE-"SEPHADEX" or synthetic polymer derivatives such as ion exchange resins.

With the covalent bonding method, where the material is immobilized by covalent bonding to a water-insoluble support, examples of particularly preferred supports include those having amino, carboxyl, sulfhydryl, hydroxy, imidazole or phenol groups which are functional groups reactive for instance with diazonium salts, acid azides, isocyanates, or active type alkyl halides.

With the support crosslinking method, where the material is immobilized to the support by covalent binding with the use of a crosslinking reagent such as glutaraldehyde, examples of particularly preferred supports include water-insoluble supports having amino groups, such as AE-cellulose, DEAE-cellulose, partially deacylated chitin, or aminoalkylated porous glass.

With the supportless crosslinking method, where immobilization is effected by crosslinking materials with a reagent having two or more functional groups, no support is particularly required. Examples of preferred crosslinking reagents include glutaraldehyde (forming a Shiff's base), an isocyanic acid derivative (forming a peptide), N,N'-ethylenebismaleimide, bis-diazobenzidine (for diazo coupling), or N,N'-polymethylenebisiodoacetamide (alkylating agent). The material which participates in the crosslinking reaction needs a suitable functional group at the N-end, such as an amino group, phenol group, sulfhydryl group or imidazole group.

With the inclusion method, the method may be classified into the lattice type in which materials to be immobilized are incorporated into fine lattices of polymeric gels, and the microcapsule type in which the antibodies or antigens are coated with semipermeable polymeric films. Examples of preferred supports in the case of the lattice type include polymeric compounds, for example, synthetic polymeric substances such as polyacrylamide gel, polyvinyl alcohol, or photocurable resin; and natural polymeric substances such as starch, konjak powder, gelatin, alginic acid, or carrageenan. In the case of the microcapsule type, various techniques are possible. When the interfacial polymerization method is used, namely the method in which the antibody is coated by utilizing the principle of polymerizing a hydrophilic monomer and a hydrophobic monomer at the interface therebetween, a nylon film based on hexamethylenediamine and sebacoyl chloride can be employed. When the drying-in-liquid method is used, namely the method in which an antibody solution is dispersed in a polymeric compound solution dissolved in an organic solvent to form an emulsion and then transferred into an aqueous solution followed by drying, thereby coating the antibody, examples of preferred supports include polymeric substances such as ethyl cellulose or polystyrene. When the phase separation method is used, namely the method in which a polymeric compound is dissolved in an organic solvent immiscible with water, an antibody is dispersed in the solution to prepare an emulsion, then a non-solvent which causes phase separation is gradually added under stirring, whereby a concentrated solution of the polymeric compound encloses the antibody droplets therearound, and subsequently the polymeric compound is precipitated to form a film which covers the antibody, is used, the above-mentioned polymeric compounds can be employed.

Labels for use in the present invention include substances which have a detectable physical, chemical or electrical property. When a detectable labeling substance is introduced, it can be linked directly such as by covalent bonds or can be linked indirectly such as by incorporation of the ultimately detectable substance in a microcapsule or liposome.

Labeling materials have been well-developed in the field of immunoassays and in general almost any label useful in such methods can be applied to the present invention. Particularly useful are enzymatically active groups, such as enzymes (see *Clin. Chem.*, (1976) 22:1232, U.S. Reissue Pat. No. 31,006, and UK Pat. 2,019,408), enzyme substrates (see U.S. Pat. No. 4,492,751), coenzymes (see U.S. Pat. No. 4,230,797 and U.S. Pat. No. 4,238,565), and enzyme inhibitors (see U.S. Pat. No. 4,134,792);,fluoresces (see Clin. Chem., (1979) 25:353); chromophores; luminescers such as chemiluminescers and bioluminescers (see U.S. Pat. No. 4,380,580); specifically bindable ligands such as biotin (see European Pat. Spec. 63,879) or a hapten (see PCT Publ. 83-2286); and radioisotopes such as $^{3}H$, $^{35}S$, $^{32}P$, $^{125}I$, and $^{14}C$. Such labels are detected on the basis of their own physical properties (e.g., fluorescers, chromophores and radioisotopes) or their reactive or binding properties (e,g., ligands, enzymes, substrates, coenzymes and inhibitors). For example, a cofactor-labeled species can be detected by adding the enzyme (or enzyme where a cycling system is used) for which the label is a cofactor and a substrate or substrates for the enzyme. Such detectable molecule can be some molecule with a measurable physical property (e.g., fluorescence or absorbance) or a participant in an enzyme reaction. For example, one can use an enzyme which acts upon a substrate to generate a product with a measurable physical property.

Any convenient immunoassay technique can be employed in the present invention including, for example, enzyme-linked immunoassay, radioimmunoassay (RIA), immunofluorescence and the use of dyes.

In enzyme linked immunoassays, an enzyme is conjugated to an antibody or antigen and the enzyme activity is measured as a quantitative label. A particularly preferred enzyme linked immunoassay is enzyme-linked immunosorbent assay (ELISA).

The enzyme may be any of the enzymes generally used in enzyme immunoassay, including maleate dehydrogenase, glucose-6-phosphoric acid dehydrogenase, glucose oxidase, peroxidase, acetylcholine esterase, alkali phosphatase, glucoamylase, lysozyme, β-D-galactosidase, etc., preferably peroxidase, alkali phosphatase or β-D-galactosidase or horseradish peroxidase.

Immunofluorescence utilizes fluorescent dyes such as fluorescein isothiocyanate or rhodamine.

The incubation steps required in carrying out the invention can be effected in a known manner, such as by incubation at temperatures of between about 20° C. and about 50° C., for between about 1 hour and about 30 hours.

Washings are typically effected using an aqueous solution such as one buffered at a pH of 6–8, preferably at a pH of about 7, employing an isotonic saline solution.

Therapeutics

Pharmaceutically acceptable salts of the above described compounds (drugs) to treat or prevent HIV-1 or HIV-2 according to the invention include those derived from pharmaceutically acceptable inorganic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, formic, benzoic, malonic, naphthalene-2-sulfonic and benezenesulfonic acids.

As used herein, the term "active ingredient" includes the compound (drug) itself, as well as a salt thereof.

Salts derived from appropriate bases include alkali metal (e.g., sodium), alkaline earth metal (e.g., magnesium), ammonium and $NR_4+$ (where R is $C_{1-4}$ alkyl) salts.

The amount of the active ingredient for use in the present invention will vary not only with the particular compound selected, but also with the route of administration, the nature of the condition being treated and the age and condition of the patient and will be ultimately determined by the discretion of the attendant physician. In general, however, a suitable dose will be in the range of less than 100 mg/kg of body weight per day.

The desired dose may conveniently be presented in a single dose or as divided doses administered at appropriate intervals, for example, at two, three, four or more sub-doses per day.

Ideally, the active ingredient should be administered to achieve peak plasma concentrations of the active ingredient of from about 1 to 75 μM, preferably about 1 to 50 μM, most preferably about 1 to about 30 μM.

While it is possible that, for use in therapy, the active ingredient may be administered as the raw chemical, it is preferable to present the active ingredient in conjunction with a pharmaceutically acceptable carrier as a pharmaceutical formulation.

The invention thus further provides for the use of a pharmaceutical formulation comprising an active ingredient together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient therefor.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active ingredient with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, nonaqueous vehicles (which may include edible oils) or preservatives.

The active ingredient may also be formulated for parental administration (e.g., by injection, for example, bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogenfree water, before use.

For topical administration to the epidermis, the active ingredient may be formulated as ointments, creams or lotions, or as a transdermal patch. Ointments and creams may, for example, be formulated with an aqueous or oil base with the addition of suitable thickening and/or gelling agents. Lotions may be formulated with an aqueous or oil base and will in general also contain one or more emulsifying agents, stabilizing agents, suspending agents, thickening agents, or coloring agents.

Formulations suitable for topical administration in the mouth include lozenges comprising an active ingredient in a flavored base, usually sucrose and acacia or tragacanth; or pastilles comprising the active ingredient in a suitable liquid carrier.

Pharmaceutical formulations suitable for rectal administration, wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration, the active ingredient may be used as a liquid spray or dispersible powder or in the form of drops.

Drops may be formulated with an aqueous or non-aqueous base comprising one or more dispersing agents, solubilizing agents or suspending agents. Liquid sprays are conveniently delivered from pressurized packs.

For administration by inhalation, the active ingredient is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the active ingredient may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient may be employed.

The pharmaceutical compositions for use according to the invention may also contain other active ingredients such as antimicrobial agents or preservatives.

The active ingredient may also be used in combination with other therapeutic agents, for example, other anti-infective agents.

The combinations referred to above may conveniently be presented for use in the form of a pharmaceutical formulation and thus the use of pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When a compound (drug) as described herein is used in combination with a second therapeutic, the dose of each compound may be either the same or different from that when the analog is used alone. The appropriate dose will be readily appreciated by those skilled in the art.

The antigens for use in the present invention can be synthetic peptides, recombinant proteins or can be derived from natural materials.

The present invention is applicable to all subtypes of HIV-1 and HIV-2.

Screening and Selecting Anti-Viral Drugs

The present invention is also directed to a method to screen and select anti-viral drugs based on the ability of a drug to inhibit the interaction (binding) between a functionally important site on a viral protein, e.g., a hepatitis viral protein, and an antibody directed against that functionally important site.

A non-limiting summary of viruses to which drugs can be screened according to the present invention is as follows:

(1) parvoviruses
(2) papovaviruses, such as papilloma virus
(3) adenoviruses
(4) herpesviruses including herpes simplex type 1 and 2, varicella-zoster virus, cytomegalovirus and EB virus
(5) poxviruses including smallpox and vaccinia
(6) picornaviruses including rhinoviruses
(7) reoviruses
(8) arboviruses including encephalitis viruses
(9) togaviruses including rubella virus and Sindbis virus
(10) arenaviruses
(11) cornaviruses
(12) retroviruses
(13) bunyaviruses
(14) orthomyxoviruses
(15) paramyxoviruses including parainfluenza virus and
(16) rhabdoviruses

Chemical Modification of Drugs

The antiviral activity of most of the substances listed in Table 1 (hereinafter) is based on their reversible binding to the V3 hypervariable loop of gp 120, resulting in inhibition of attachment of antibodies specific for this loop and in antiviral activity. The efficiency of binding of such substances can be increased by shifting the equilibrium between bound and unbound antiviral drugs towards the bound drugs by chemically modifying the drugs. This can be accomplished by incorporating into such drugs active groups which are expected to react with the protein moiety of the V3 hypervariable loop (i.e., available amino and carboxyl group). This can be accomplished, for example, by incorporating into the antiviral compounds carbonyl chloride groups (replacing carboxyl groups) or by using carboxylic acid anhydrides. A similar effect can be accomplished by using the antiviral drugs in the form of aldehydes expected to react with available amino groups on the V3 hypervariable loop. Examples for such substances are shown in Table 1 (i.e., substances #93 and #106).

The invention will now be described with reference to the following non-limiting examples.

EXAMPLES

Example 1: Double Antibody Radioimmunoassay (RIA) and Enzyme-Linked Immunoadsorbent Assay (ELISA) Tests Wells of 96 well polystyrene plates (Immulon 2, Dynatech Laboratories, Inc., Chantilly, Va.) were coated with synthetic peptides (200 μl; 20μg/ml in 0.1 M Tris-HCl, pH 8.8) overnight at 20° C. The peptides were from the sequence of HIV-1, clone BH 10 envelope glycoproteins gp120 and gp41 (Neurath, A. R., Strick, N., and Lee, E. Y. S. (1990), "B-cell Epitope Mapping of Human Immunodeficiency virus (HIV-1) Envelope Glycoprotein with Long (19 to 36-residue) Synthetic Peptides", *J. Gen. Virol.*, 71., 85–95) and from V3 hypervariable loops of 21 distinct HIV-1 isolates (clones) Neurath, A. R., and Strick, N., (1990), "Confronting the Hypervariability of an Immunodominant Epitope Eliciting Virus Neutralizing Antibodies from the Envelope Glycoprotein of the Human Immunodeficiency Virus Type 1 (HIV-1)", *Molec. Immunol.*, 27, 539–549. The latter peptides corresponded to full-length V3 loops generated by disulfide bonds between N- and C- terminal cysteine residues. After washing with 0.14 M NaCl, 0.01 M Tris, 0.02% $NaN_3$ (TS), the wells were postcoated with a mixture of bovine serum albumin (BSA) and gelatine (10 and 2.5 mg/ml, respectively) in TS. BSA was omitted from the postcoating solution for RIA tests in which antibodies to ATA were used. Polystyrene plates coated with recombinant gp120 and gp160, respectively, (500 ng/well; from American Bio-Technologies, Inc., Cambridge, Mass. and MicroGeneSys, Inc., West Haven, Conn., respectively) were also used for RIA and ELISA tests.

To define sites on gp120/gp41 reacting with ATA, the inhibitory effect of this compound was studied by RIA tests using gp120- and gp160-coated wells, respectively, and antisera (final dilutions 1:150) against synthetic peptides from the entire sequence of gp120/gp41 of HIV-1 BH 10. The preparation and biological properties of these antisera were described elsewhere (Neurath et al., (1990), *J. Gen. Virol.*, 71, 85–95). Each of the antisera was diluted in a mixture of fetal bovine serum and goat serum (9:1) containing 0.1% Tween 20, adjusted to pH 8. ATA (final concentration 50 μg/ml) was added in one set of assays, but was omitted from a parallel set. After incubation overnight at 25° C., the plates were washed with TS. Attached rabbit IgG was detected using $^{125}$I-labeled anti-rabbit IgG, as described before (Neurath et al., 1990, *J. Gen. Virol.*, 71, 85–95). Similarly, the inhibitory effect of ATA on the reaction of peptides derived from gp120/gp41 and of peptides derived from V3 hypervariable loops from gp120 of distinct HIV-1 isolates with the respective homologous anti-peptide antisera was studied. In the latter case, antisera were diluted 1:1,000 for the assays.

Monoclonal antibodies (McAbs) recognizing the V3 hypervariable loop of HIV-1 BH 10 (McAb 9305 from DuPont, Wilmington, Del.) and an antiserum from a chimpanzee immunized with a mixture of V3 hypervariable loop peptides from 21 distinct HIV1 isolates (Girard, M., Kieny, M-P., Pinter, A., Barre-Sinoussi, F., Nara, P., Kolbe, H., Kusumi, K., Chaput, A., Reinhart, T., Muchmore, E, Ronco, J., Kaczorek, M., Gomard, E, Gluckman, JC., Fultz, P. N. (1991), "Immunization of Chimpanzees Confers Protection Against Challenge with Human Immunodeficiency Virus", *Proc. Natl. Acad. Sci. USA*, 88, 542–546) were also used for studies on the inhibitory affect of ATA on the reaction between these antibodies and gp120, using ELISA tests. These tests were carried out similarly as RIA, except that sodium merthiolate (1 mg/ml) was added to the buffers instead of $NaN_3$, and goat antimouse IgG antibodies (Boehringer Mannheim Biochemicals, Indianapolis, Ind.) and goat anti-human IgG antibodies (Sigma, St. Louis, Mo.), respectively, each linked to horseradish peroxidase were used as second antibodies at final dilutions of 1:1,000 in phosphate-buffered saline (PBS) containing 10% goat serum and 0.1% Tween 20. After incubation for 2 hours at 37° C., the wells were washed with PBS and peroxidase activity was determined using a kit from Kirkegaad & Perry Laboratories, Inc., Gaithersburg, Md. Absorbance at 450 nm was determined in an MR600 Microplate reader (Dynatech Laboratories, Inc.).

The inhibitory effect of ATA and of other compounds on the reaction between antibodies with predetermined specificity and gp120 (or synthetic peptides derived from it) was determined from the formula:

$$\frac{\text{(counts of radioactivity (cpm) in the absence of } ATA) - \text{(cpm in the presence of } ATA)}{\text{cpm in the absence of } ATA} \times 100.$$

An analogous formula was used to calculate the percentage of inhibition from optical density readings resulting from ELISA tests.

Chemicals other than ATA were screened for inhibitory activity essentially as described above. First each of the chemicals (at final concentrations of 60 and 180 μg/ml, respectively, prepared by diluting a stock solution [10 mg/ml in dimethylsulfoxide]) were screened for inhibitory activity in the reaction between antibodies to a peptide from the V3 hypervariable of HIV-1 BH 10 (peptide (303–338); Neurath et al., (1990), *J. Gen. Virol.*, 71, 85–95; Neurath and Strick, (1990), *Molec. Immunol.*, 27, 539–549) and gp120. Chemicals found positive during the first screening were also assayed for inhibitory activity in the reaction between: (1) 125 ng McAb 9305 and gp120; (2) chimpanzee anti-V3 antiserum (diluted 1:1,000) and gp120 and (3) rabbit antiserum to the V3 loop of HIV-1 BH 10 and the homologous peptide (303–338). Chemicals with inhibitory activity established by the respective immunoassays were screened further for antiviral activity.

Commercially available ATA is a mixture of monomers and polymers of distinct molecular masses (Gonzalez et al., (1979) *Biochem. Biophys. Acta,* 562, 534–545); Cushman et al., (1991), *J. Chem.,* 34, 329–337). The monomers [molecular mass (M.W.)=422.4 daltons] were separated from the polymers. ATA (20 mg/ml in the form of free acid neutralized with 0.4 M NaOH) was dialyzed against $H_2O$ in a dialysis membrane with a molecular mass cutoff of 500 daltons. The inhibitory activities of the original ATA preparation and of the retentate, consisting of polymers of ATA and representing 17.6% of the original ATA before dialysis (established by measurements of optical density at 306 mm) were compared by RIA.

Example 2: Preparation of antiserum to ATA

ATA was linked to BSA essentially as described by Van Regenmortel, M. H. V., Briand, J. P., Muller, S., and Plaue, S. (1988), *Synthetic Polypetides as Antigens.* Elsevier, Amsterdam, pp. 105–106. Briefly, 2 ml of a solution ATA (2.5 mg/ml) in distilled water was mixed with BSA (final concentration 2.5 mg/ml) and to this 10 mg of 1-ethyl-3-(3-dimethylaminopropyl) carbodimide hydrochloride (EDC; Pierce, Rockford, IL) was added. ATA in the form of free acid neutralized to pH 7 by NaOH was used for the coupling procedure. After mixing for 10 minutes at room temperature, the product was dialyzed against PBS to remove unreacted EDC. Two NZW rabbits were immunized with the ATA-BSA conjugate (400 μg) in combination with complete Freund's adjuvant. The rabbits were boosted with 400 μg doses of the conjugate in combination with incomplete Freund's adjuvant at intervals of two weeks. Two weeks after each immunization, samples were taken and analyzed for antibodies by RIA. Ten weeks after the initial immunization, the rabbits were sacrificed after collection of blood by cardiac puncture.

Antibodies to ATA were detected by double antibody RIA using wells coated with an ATA-ovalbumin conjugate. This conjugate was prepared in the same way as described for the ATA-BSA conjugate. Dilution endpoints of anti-ATA antibodies, determined as described by Ritchie, D. G., Nickerson, J. M., and Fuller, G. M. (1983), "Two Simple Programs for the Analysis of Data from Enzyme-linked Immunosorbent Assays (ELISA) on a Programmable Desk-top Calculator," *Methods in Enzymology,* 92, 577–588) of the two antisera were: 1:2,700 and 1:150,000, respectively. The second antiserum was used for subsequent RIA tests.

To demonstrate binding to gp120 and to the (303–338) V3 hypervariable loop peptide from HIV-1 BH 10, ATA (final concentration 20 μg/ml) in TS containing 1 mg/ml of gelatin was added to the antigen-coated wells. ATA was also added to a control peptide, (518–542), and to wells coated with gelatin only. After incubation for 4 hours at 20° C., excess ATA was removed, the wells were washed with TS and attached ATA was determined by double-antibody RIA using serial dilutions of the anti-ATA antiserum. Similar tests were carried out with serum from the same rabbit before immunization with the ATA-BSA conjugate; the corresponding results (100–450 cpm) were subtracted from cpm corresponding to RIA results obtained with the anti-ATA antiserum. For additional assays aimed at determining the binding of ATA to synthetic peptides from gp120 and gp41 of HIV-1 BH 10 and to V3 hypervariable loop peptides from 20 additional HIV-1 isolates, anti-ATA antiserum was used at a final dilution of 1:800.

Example 3: ATA Attaches to the v3 hypervariable Loop of Distinct HIV-1 Isolates

Figure 1C:
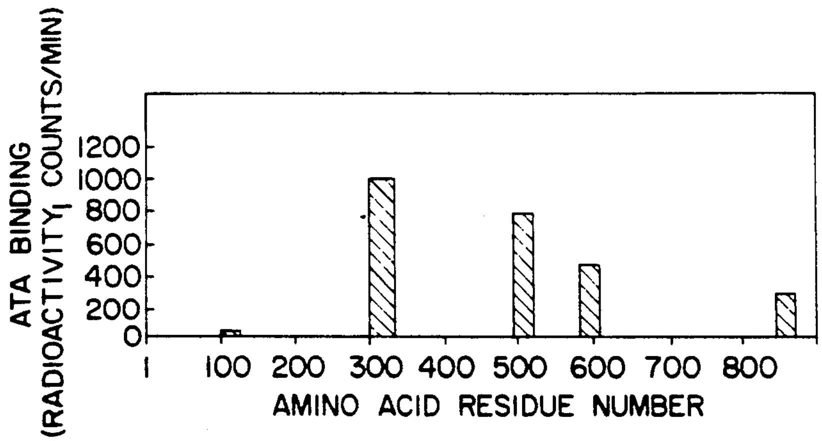
Figure 1B:
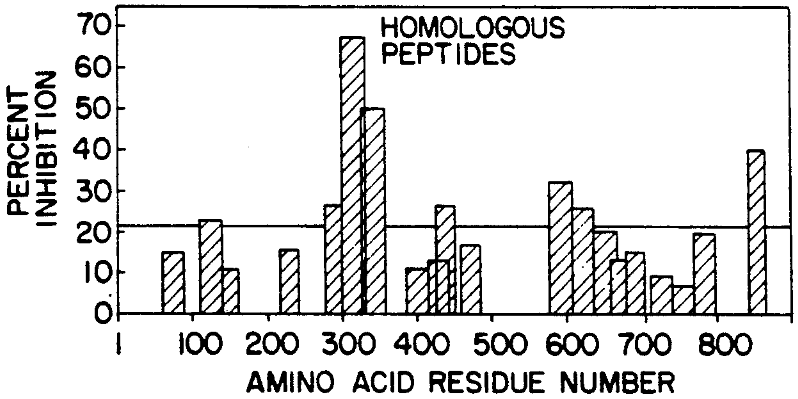
Figure 1A:
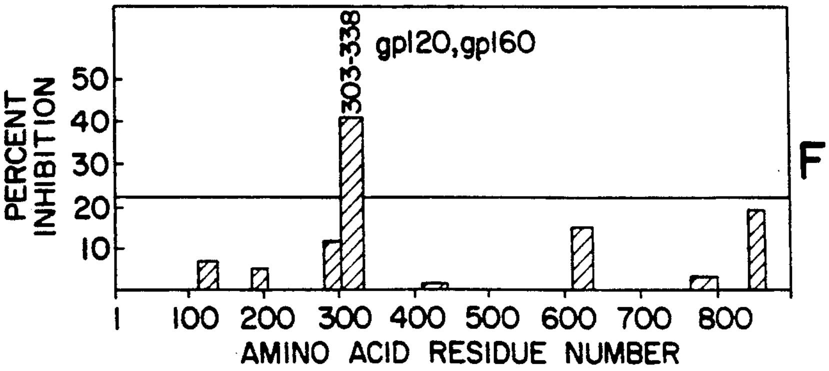

Earlier studies established that ATA reacted with HIV-1 gp120 expressed on the surface of infected cells (Schols et al., (1989) supra; Schols et al (1990), supra). The precise localization within the sequence of gp120 of the attachment site for ATA may help explain the mechanism of action of this antiviral substance. For this reason, experiments were designed to accomplish this goal. It was considered possible that attachment of ATA to specific sites on gp120 might interfere with the attachment of site-specific antibodies to overlapping determinants. The availability from earlier studies of antipeptide antibodies with predetermined specificity against distinct segments of gp120 (Neurath et al., (1990), *J. Gen. Virol.,* 71, 85–95) made it possible to test this hypothesis experimentally. At the same time it was also of interest to determine whether or not ATA may also attach to regions of the smaller HIV-1 envelope glycoprotein gp41. The reaction of 34 anti-peptide antisera directed against distinct portions of the gp120/gp41 sequence with recombinant gp120 (gp160) in the presence and absence of ATA was studied by double antibody RIA. ATA significantly (≧22%) inhibited the attachment to gp120 of antibodies against the (303–338) segment of this glycoprotein, corresponding to the V3 hypervariable loop (Modrow, S., Hahn, B. H., Shaw, G. M., Gallo, R. C., Wong-Stall, F., Wolf, H. (1987), "Computer-assisted Analysis of Envelope Protein Sequences of Seven Human Immunodeficiency Virus Isolates; Prediction of Antigenic Epitopes in Conserved and Variable Regions," *J. Virol.,* 61, 570–578) (FIG. 1A).

The recombinant glycoproteins gp120 and gp160 from HIV-1, clone BH 10, were obtained from a baculovirus expression system and were glycosylated. Similar results were obtained with gp120 HIV-1 SF2 expressed in a baculovirus expression system, but not with gp120 of the same virus subtype expressed in *E. coli* and therefore non-glycosylated (data not shown). These results suggested that the interaction of ATA with gp120 was influenced by glycosylation of this protein.

In order to establish whether or not ATA reacted with the protein moiety gp120, the reaction of synthetic peptides from the entire gp120/gp41 sequence with homologous anti-peptide antibodies in the presence and absence of ATA was studied. The reaction between the V3 hypervariable loop peptide (303–338) and antibodies against it was most dramatically inhibited by ATA. Inhibition was also observed with other peptides, most significantly with the peptide (331–361), partially overlapping the V3 hypervariable loop, and with the peptide (845–862) from gp41 (FIG. 1B). Thus the protein moiety of gp120 appeared to be involved in interaction with ATA.

Figure 2:
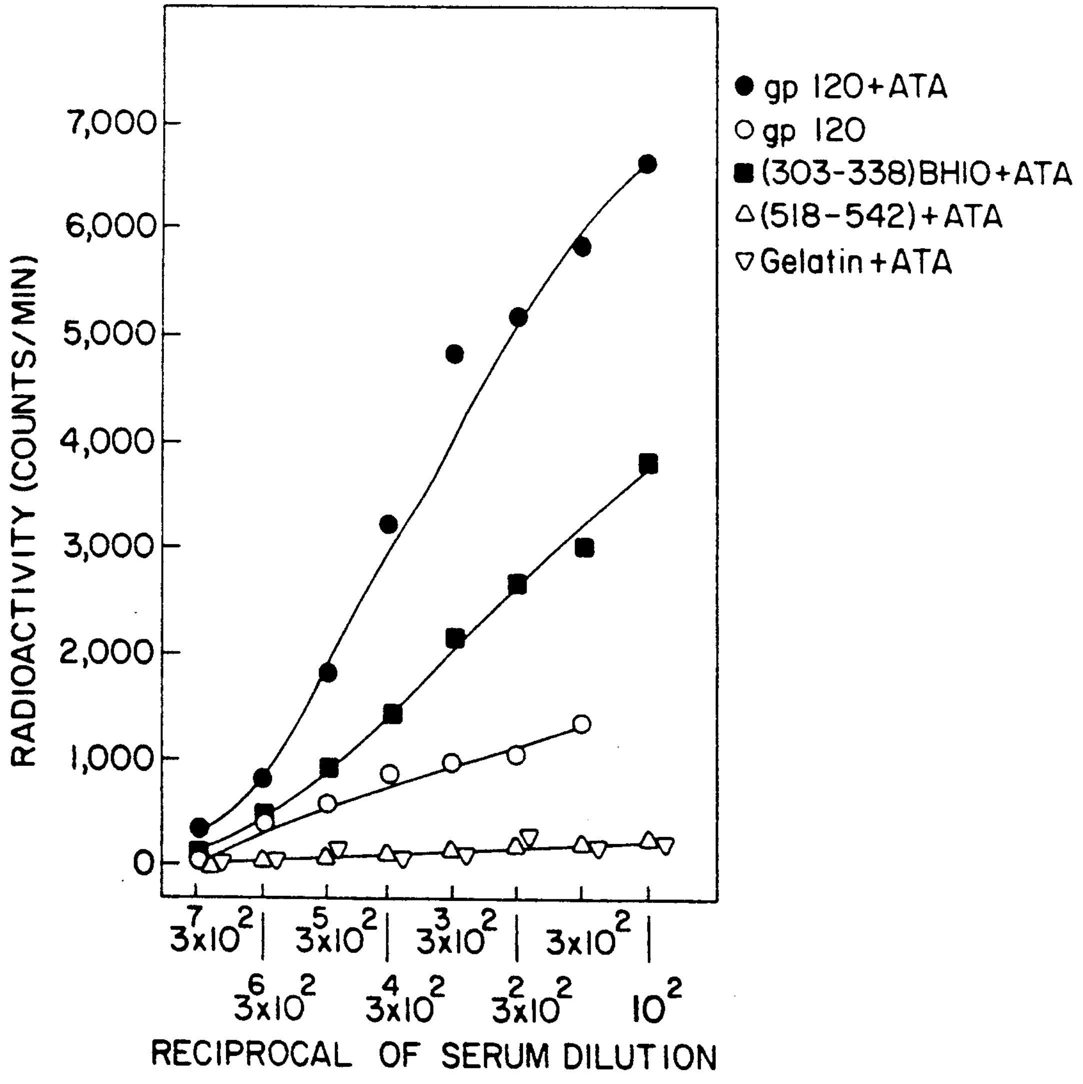
FIG. 2 is a graph depicting the recognition by antibodies (generated by immunization with an aurintricarboxylic acid (ATA)bovine serum albumin (BSA) conjugate) of ATA specifically attached to gp120 or to the V3 hypervariable loop peptide (303–338). gp120-coated wells not pre-exposed to ATA, gelatin-coated wells or wells coated with another peptide from HIV gp41, (518–542), both pre-exposed to ATA (50 μg/ml), served as controls (*Vaccines* 91 (eds. R. M. Chanock, H. S. Ginsberg, F. Brown, and R. A. Lerner), Cold Spring Harbor Laboratory press, (1991), p.20).

These results provided evidence for the preferential inhibition by ATA of the reaction between the V3 hypervariable loop and the corresponding antibodies. However they did not establish whether ATA reacted with gp120 or with antibodies directed against the V3 hypervariable loop. In order to formally establish that ATA attached to gp120, additional experiments were designed to demonstrate directly the binding of ATA to gp120 and to defined portions thereof. To accomplish this, first antibodies directed against the hapten ATA were prepared. The anti-ATA antibodies reacted with gp120 and with the hypervariable loop peptide (303–338), each preincubated with ATA, but not with gelatin or a control peptide (518–542) preincubated with ATA (FIG. 2). The antibodies did not react with the peptide (303–338) itself but reacted with gp120 to a much lesser extent than with gp120 pretreated with ATA. The reason for the apparent partial cross-reactivity between ATA and gp120 is not known but it is possible that anti-idiotypic antibodies generated during immunization with ATA would recognize the ATA binding site on gp120. After establishing that ATA reacted with gp120 and the V3 hypervariable loop peptide (FIG. 2), it was of interest to establish whether or not other peptides from the gp120/gp41 sequence would also react with ATA. The reaction of 34 distinct peptides from the entire gp120/gp41 sequence with ATA was studied using anti-ATA antibodies as an indicator system to prove binding. The peptide (303–338) was the most efficient binder of ATA, followed by peptides (492–518), (579–611) and (845–862) (FIG. 1C). Paradoxically, ATA bound to the peptide (492–518), corresponding to the C-terminus of gp120, but did not inhibit the reaction between this peptide and homologous anti-peptide antibodies (compare FIG. 1B with FIG. 1C).

Since ATA has a net negative electric charge, the possibility had to be considered that electrostatic forces contributed to the reaction between ATA and positively charged segments (peptides) from gp120/gp41. Therefore, the net electric charges of distinct synthetic peptides from gp120/gp41 were calculated and plotted in FIG. 1D. It is evident that peptides (303–338), (492–518) and (845–862) reacting with ATA were the most positively charged. However, the correlation between positive charge and reactivity with ATA was not absolute. Although a net positive electric charge appears to be a prerequisite for reactivity with ATA, the negative charge of organic compounds is not a sufficient requirement for their inhibitory activity on V3 loop-antibody reactions, or for antiviral activity, as will be shown further.

Figure 3:
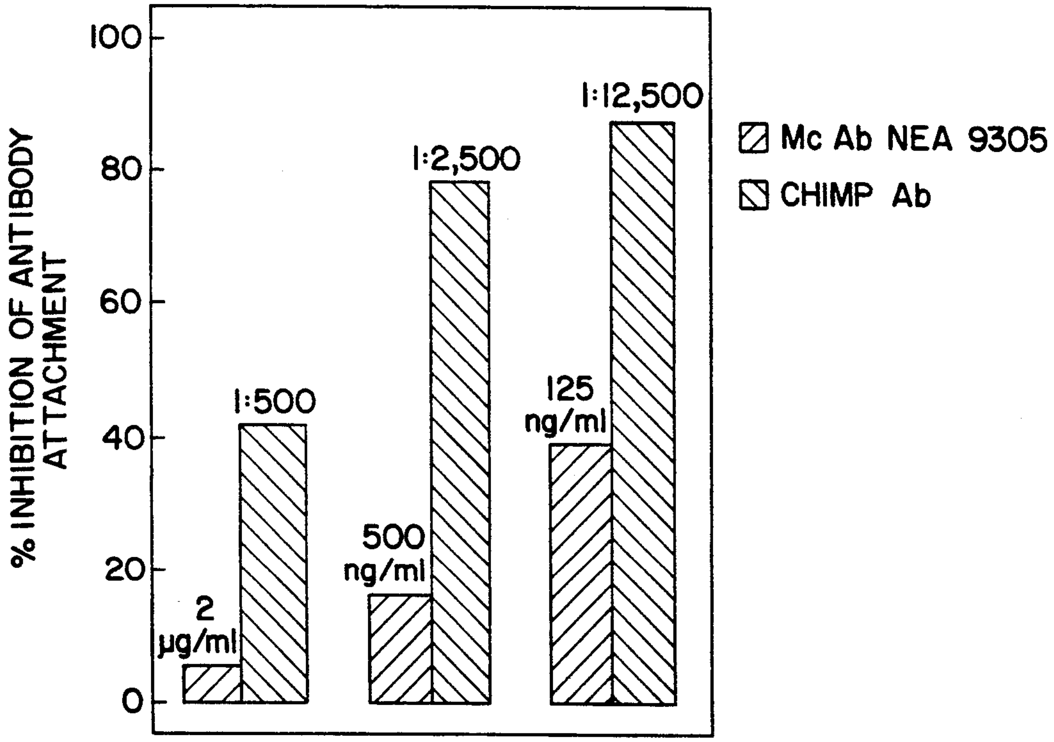
FIG. 3 is a graph showing the inverse correlation between the inhibitory effect of ATA (used at a constant final concentration of 50 μg/ml) and the concentration of antibodies reacting with gp120 immobilized on wells of polystyrene plates. The final concentration of antibodies (McAb 9305) and the dilution of the chimpanzee antiserum, respectively, are indicated on the top of the bars.

The extent of inhibition by ATA of the reaction between gp120 and antibodies specific for the V3 hypervariable loop correlated with the dilution of antibodies (FIG. 3), suggesting competition between site-specific antibodies and ATA for overlapping attachment sites. In addition to McAb NEA 9305, specific for the V3 hypervariable loop and chimpanzee anti-gp120 antibodies predominantly specific for this loop (Girard et al., (1991), *Proc. Natl.Acad. Sci USA*, 88, 542–546), results similar to those presented in FIG. 2 were obtained with other monoclonal antibodies and with human anti-HIV-1 positive sera reacting with V3 hypervariable loop peptides from a series of HIV-1 isolates.

Figure 4B:
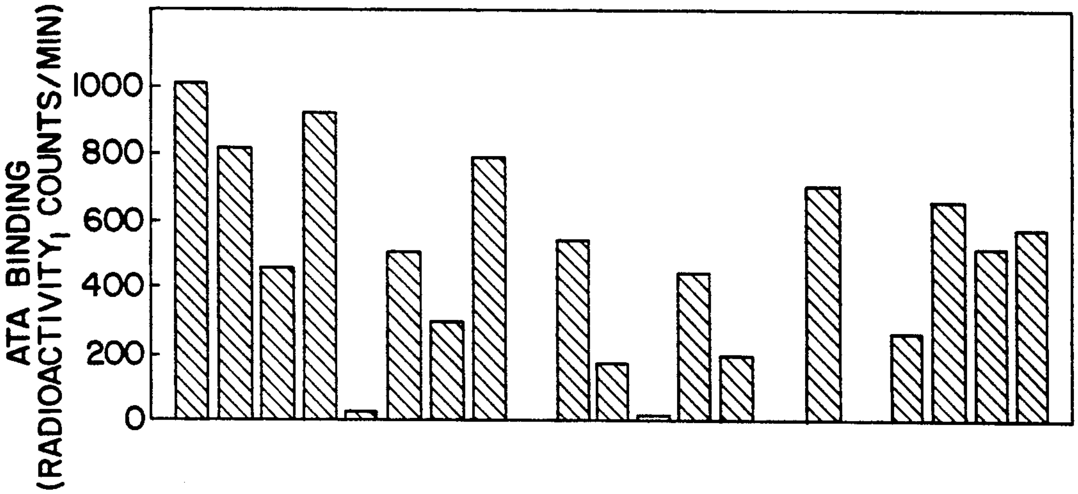
FIG. 4B: attachment of ATA to distinct V3 hypervariable loop peptide-coated wells as determined by double antibody RIA using rabbit antiserum against ATA.
Figure 4A:
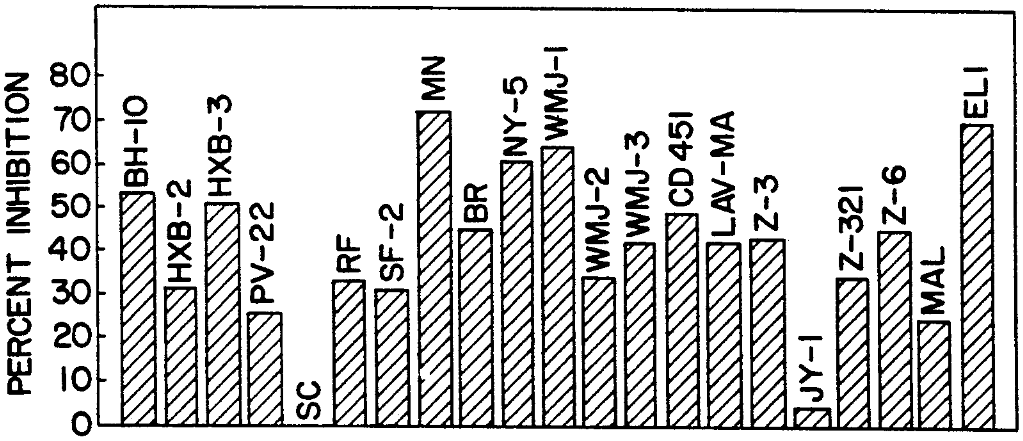
FIG. 4A: Inhibitory effects of ATA (50 μg/ml) on the reaction between peptide-coated wells and homologous anti-peptide antisera (diluted 1:1,000).

The antiviral activity of ATA (Schols et al., (1989), supra; Schols et al; (1990) supra; Cushman et al., (1991), J. Med. Chem. 34, 329–3337) and its reactivity with gp120 has been demonstrated for selected numbers of HIV-1 subtypes. Therefore, it appeared necessary to determine whether or not ATA reacted with V3 hypervariable loops of a wider array of HIV-1 isolates (clones). To accomplish this, the inhibitory effect of ATA on the reaction between V3 hypervariable loop peptides from 21 distinct HIV-1 isolates (clones) with homologous antibodies was investigated. The attachment of ATA to the corresponding synthetic peptides using anti-ATA antibodies was also studied. The results (FIG. 4) indicate differences in reactivity of ATA with distinct V3 hypervariable loop peptides. The reactivity of ATA appeared to be minimal with hypervariable loop peptides corresponding to HIV-1 SC and JY-1 sequences. There was no absolute correlation between the inhibitory effect of ATA on antigen-antibody reactions and the attachment of ATA to the distinct loop peptides, as determined by subsequent anti-ATA antibody binding. These differences may be explained by distinct binding constants for the reaction between ATA and the respective synthetic peptides, since ATA was present in the reaction mixture when competition between the compound and antibodies was studied (FIG. 4A), but was removed from peptide-coated wells before the addition of anti-ATA antibodies used as a marker to demonstrate ATA-peptide binding (FIG. 4B). Although the net electric charge of the SC peptide, which bound very little ATA, was +2 and the net electric charge of the BH 10 peptide, which bound the highest levels of ATA (FIG. 4B), was +8, there was no general correlation between the extent of ATA binding and the net positive electric charge of peptides.

Portions of ATA in commercial preparations of the compound are in the form of polymers of graded molecular masses. The antiviral potency of ATA wa directly correlated with the molecular weight of the polymers (Cushman et al., (1991), *J. Med. Chem.*, 34, 329–337). The antiviral effect of these polymers could be explained by their inhibitory effect on HIV-1 reverse transcriptase (Gonzalez et al, (1979), *Biochem. Biophys. Acta,* 562, 534–545; Cushman et al, (1991), J. Med. Chem., 34, 329–337).

Figure 5:
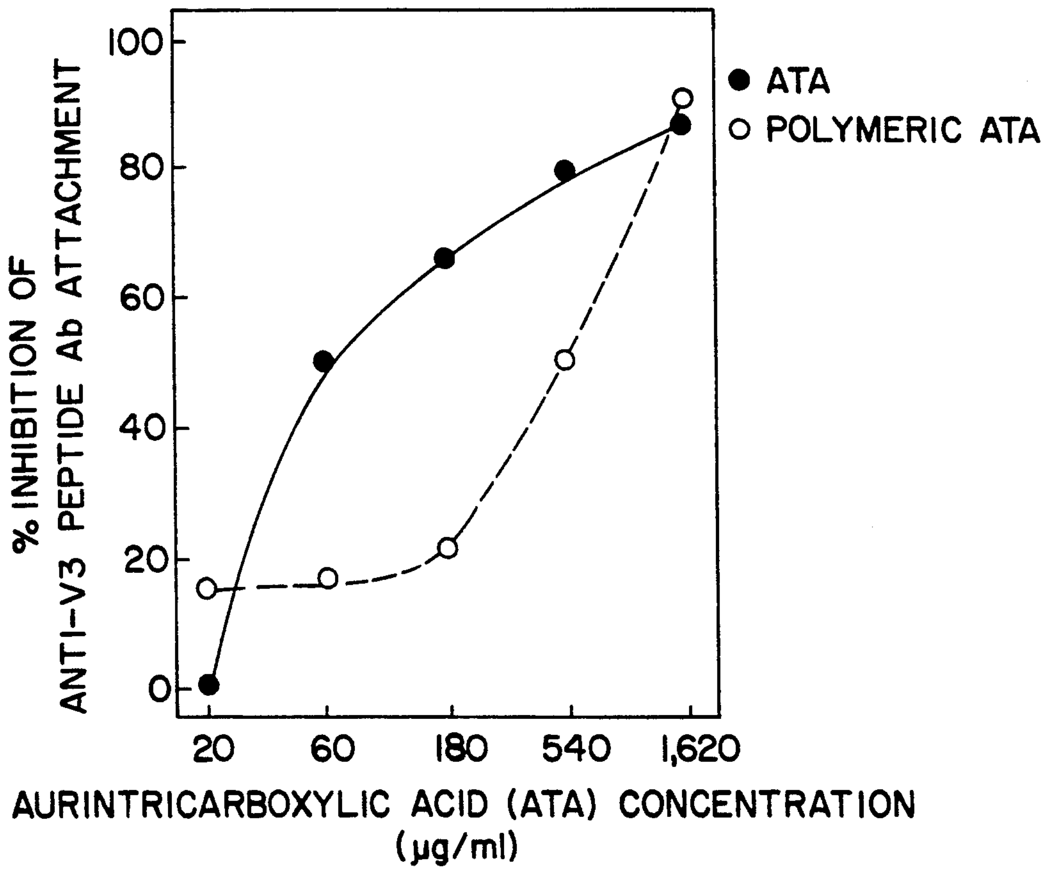
FIG. 5 is a graph showing the inhibitory effect of aurintricarboxylic acid (ATA) and of polymeric ATA on the attachment of antibodies, raised by immunization with the peptide corresponding to the entire sequence of the V3 hypervariable loop of gp120 BH10, to wells coated with the corresponding gp120 glycoprotein. ATA monomers [molecular mass (M.W.)=422.35 daltons] were separated from polymers by dialysis through M.W.=500 cutoff membranes.
Figure 6:
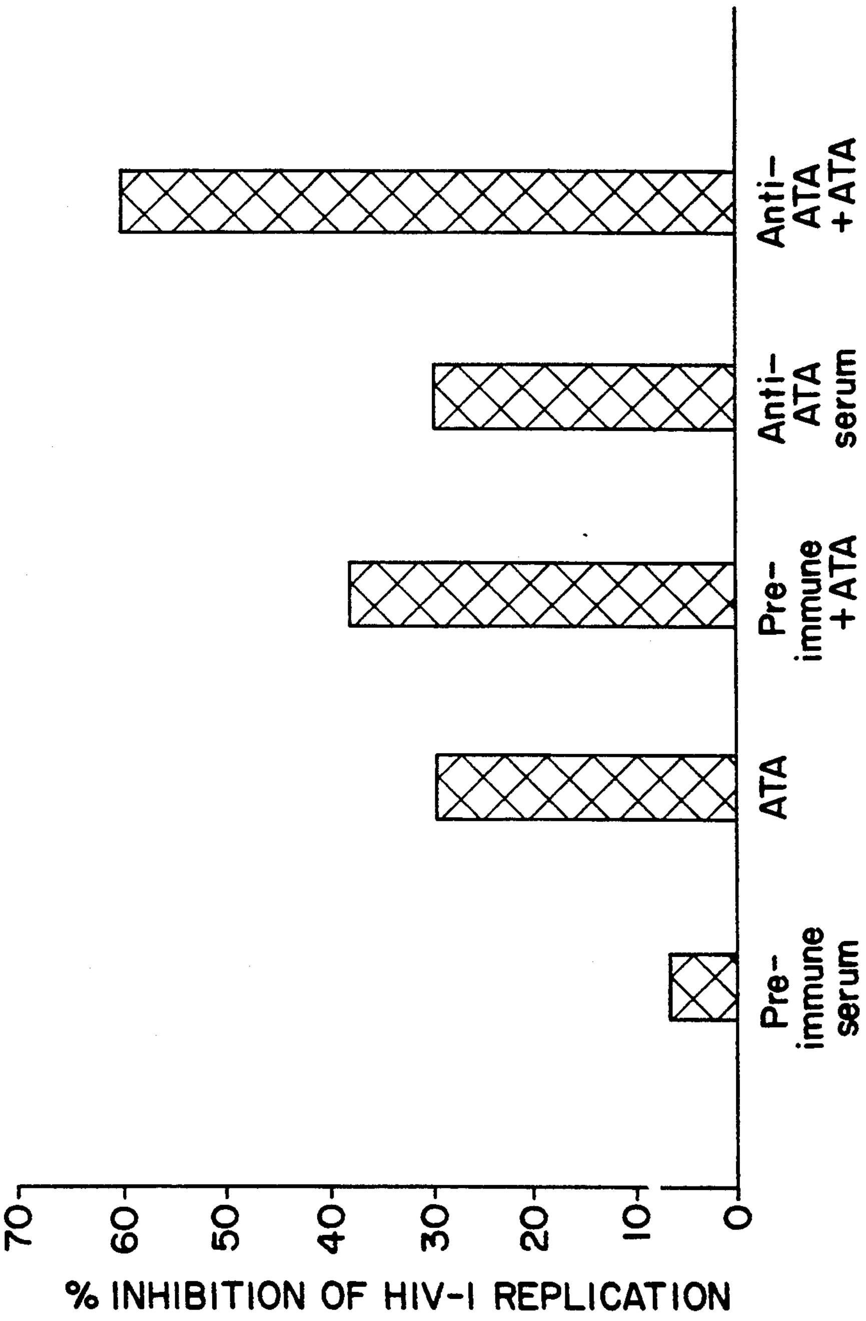
FIG. 6 is a graph indicating that an antiserum to ATA can enhance the antiviral effect of ATA. In this graph the effect of preimmune serum; of ATA alone (5 μg/ml); the inhibitory effect of preimmune serum plus ATA; the inhibitory effect of the anti-ATA antiserum and the inhibitory effect of the anti-ATA antiserum together with ATA are compared. It is evident from the graph that anti-ATA alone has some inhibitory activity on the replication of the human immunodeficiency virus type 1. The compound effect of ATA and anti-ATA is higher than that of ATA or of anti-ATA alone. Anti-ATA was used at a 1:15 dilution.

To determine the relative contribution of high and low molecular mass forms of ATA to the observed inhibitory activity on V3 hypervariable loop-antibody reactions, ATA was dialyzed against water using dialysis membranes with a molecular mass cutoff of 500 daltons. Original ATA and the retentate, expected to contain higher molecular weight polymers, were compared for inhibitory activity in the reaction between gp120 and antibodies to the V3 hypervariable loop peptide (303–338). Results in FIG. 5 indicate that the higher molecular weight forms of ATA were less inhibitory than the original ATA preparation. This suggested that ATA monomers reacted with the V3 hypervariable loop of HIV-1 gp120 and were involved in antiviral activity resulting from blocking of biologically important sites within this loop. This conclusion was essential for the search and synthesis of other compounds expected to exert their antiviral effects by attachment to the V3 hypervariable loop of gp120.

Example 4: Screening of Chemicals, Preselected for Inhibitory Activity in Site-specific RIA (ELISA), for Antiviral Activity All chemicals were tested at serial two-fold dilutions (1.25–80 μg/ml, prepared from a stock solution containing 10 mg/ml in dimethylsulfoxide). The chemicals were obtained from Aldrich, Milwaukee, Wis. or were synthesized. Their inhibitory activity was determined by two distinct methods, based on inhibition of synthesis of core protein P24 and on protection by the chemicals of cells against the cytopathic effect of HIV-1 (colorimetric method) respectively.

The chemicals were serially diluted in RPMI 1640 medium without phenol red (GIBCO, Grand Island, N.Y.) containing 10% fetal calf serum (FCS). Aliquots of the diluted solutions were added to wells of 96 well plates and mixed with an equal volume of diluted HIV-1

[multiplicity of infection (MOI) =0.0045]. After incubation for 1 hour at 37° C., 25 μl of polybrene (1 μg/ml) treated MT-2 cells (Harada, S., Koyanagi, Y., Yamamoto, N., (1985), "Infection of HTLV-III/LAV in HTLV-I-carrying Cells MT-2 and MT-4 and Application in a Plaque Assay", *Science,* 229, 563–566), (5,000 cells/well) were added. The mixture was incubated for 1 hour at 37° C. and the volume was adjusted with RPMI 1640 medium with 10% FCS to 200 μl. On the fourth day after incubation at 37° C., 100 μl of culture supernatants were collected from each well and equal volumes of fresh medium were added to the wells. The supernatants were assayed for P24 using a kit from Coulter Immunology (Hialeah, Fla.). On the sixth day, an indicator XTT tetrazolium dye (1 mg/ml; 50 μl/well; PolySciences, Inc., Warrington, Penna.) was added to the cells. After 4 hours, intracellular formazan was determined colorimetrically at 450 nm.

Example 5

Figure 7A:
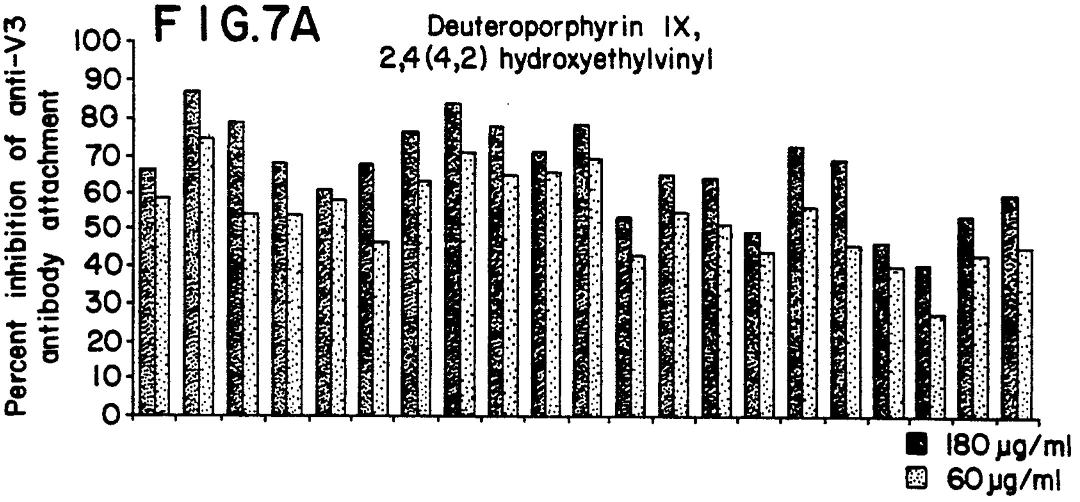
FIGS. 7A and 7B are bar graphs depicting the inhibitory effect of deuteroporphyrin IX,2,4 (4,2) hydroxyethylvinyl (FIG. 7A) and of meso-tetra(4-carboxyphenyl)porphine (FIG. 7B) on the reaction of full-length V3 hypervariable loop peptides from gp120 from 21 distinct HIV-1 isolates (clones) with homologous anti-peptide antisera. Peptide coated wells of polystyrene plates were reacted in the presence and absence of the inhibitory compounds with the respective rabbit antisera diluted 1:1,000, and the attachment of rabbit IgG was subsequently determined using $^{125}$I-labeled anti-rabbit IgG.
Figure 7B:
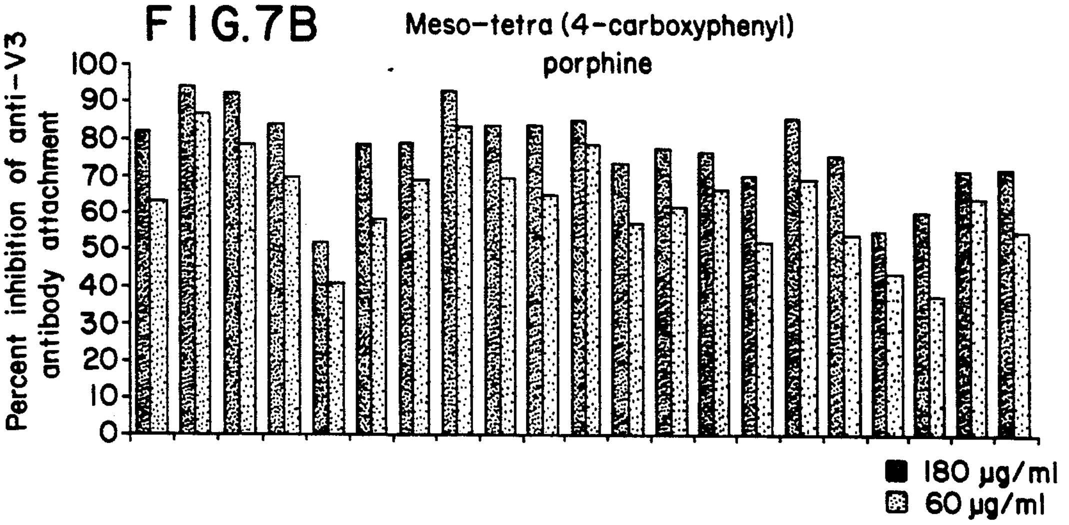

Since porphyrin derivatives (substances #146 through #168 in Table 1) represent a class of substances having several members with anti-HIV-1 antiviral activity, it was of interest to determine whether or not selected substances from this group would inhibit the reaction of V3 hypervariable loop peptides corresponding to distinct HIV-1 isolates with the corresponding homologous antibodies. Two of the substances were selected for these experiments, namely, deuteroporphyrin IX, 2,4(4,2) hydroxyethylvinyl and meso-tetra(4-carboxyphenyl)porphine. Each of these compounds inhibited the interaction between V hypervariable loop peptides and homologous antibodies corresponding to all 21 HIV-1 isolates (clones) tested (FIG. 7A and FIG. 7B). Thus, it is expected that porphyrin derivatives shown to have inhibitory activity against HIV-1 IIIB will have similar antiviral activities against other HIV-1 isolates.

Figure 7C:
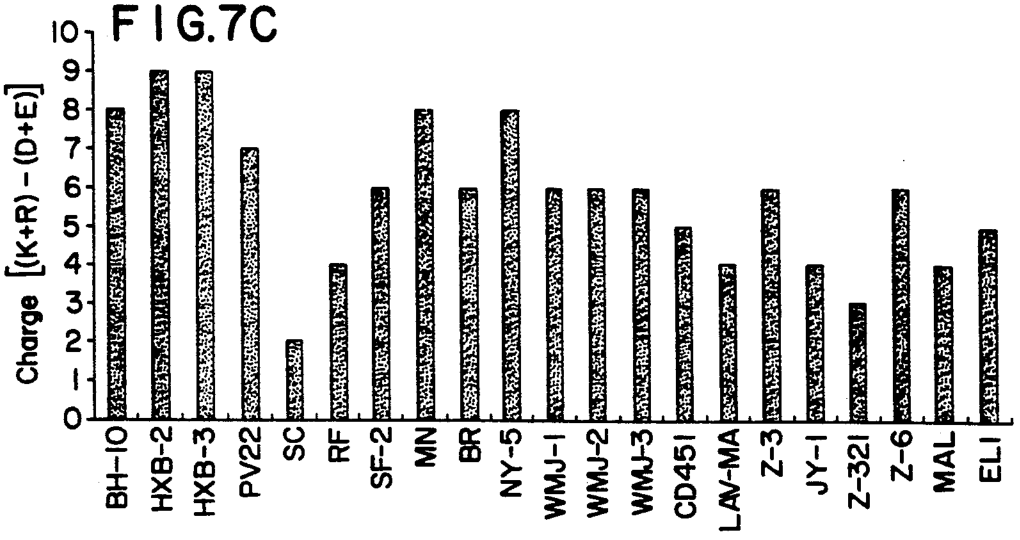
FIG. 7C is a bar graph depicting the net electric charge of the peptides, determined by subtracting the number of aspartic (D) and glutamic (E) acid residues from the sum of lysine (K) and arginine (R) residues.

Without wishing to be bound by any particular theory of operability, the inhibitory effect of these substances may be to some extent related to the net electric positive charge of V3 hypervariable loop. For example, meso-tetra (4-carboxyphenyl) porphine had a relatively low inhibitory activity on the reaction of antibodies with the V3 peptide from HIV-1 SC having a charge of +2 as compared for example with HXB-2 and HXB-3 V3 peptides having an electric charge of +9 (FIG. 7C). However, there was no direct correlation between the inhibitory effect of the two porphyrin derivatives listed and the net electric charge of distinct V3 peptides.

Figure 8:
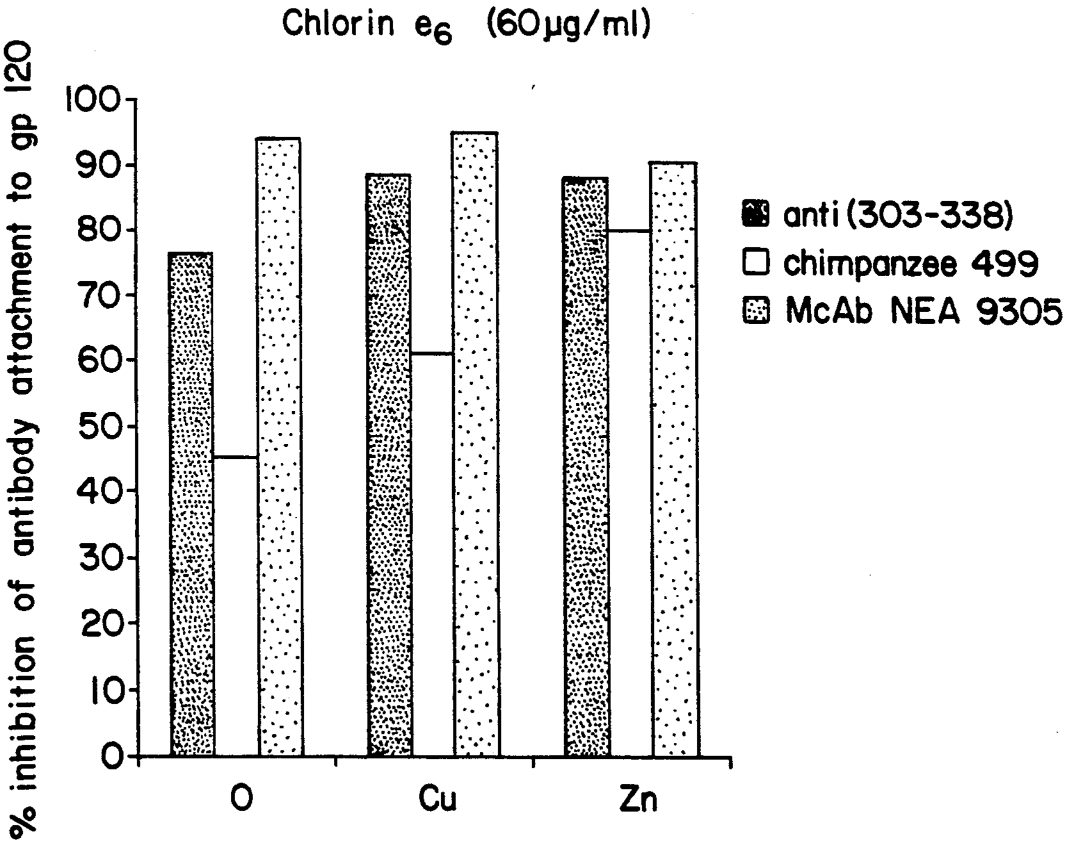
FIG. 8 is a bar graph depicting the inhibitory effect of chlorine$_6$ (60 μg/ml) and metal chelates thereof on the reaction between HIV-1 IIIB glycoprotein gp120 and three distinct antibodies reacting with the V3 hypervariable loop of this glycoprotein. The antisera used were rabbit antiserum to a synthetic peptide corresponding to the V3 hypervariable loop of HIV-1 clone BH10, serum of a chimpanzee immunized with V3 hypervariable loop peptides of distinct HIV-1 isolates and monoclonal antibodies (McAb NEA 9305) raised against residues (315–329) of the V3 hypervariable loop of HIV-1 BH10 (Neurath et al (1990), Molec. Immunol., 27, 539–549).
Figure 9:
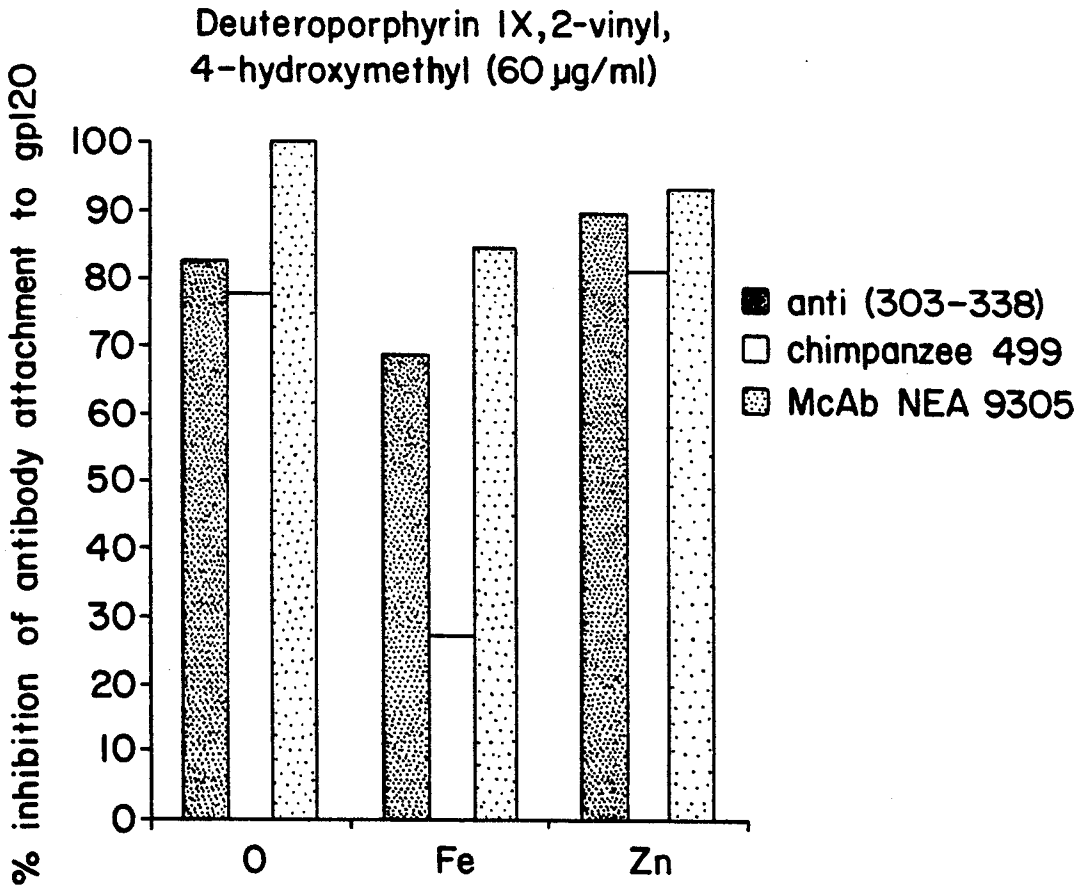
FIG. 9 is a bar graph depicting the inhibitory effect of deuteroporphyrin IX,2-vinyl,4-hydroxymethyl (60 μg/ml) and metal chelates thereof on the reaction between HIV-1 IIIB glycoprotein gp120 and three distinct antibodies reacting with the V3 hypervarible loop of this glycoprotein. The antisera used were rabbit antiserum to a synthetic peptide corresponding to the V3 hypervariable loop of HIV-1 clone BH10, serum of a chimpanzee immunized with V3 hypervariable loop peptides of distinct HIV-1 isolates and monoclonal antibodies (McAb NEA 9305) raised against a synthetic peptide corresponding to residues (315–329) of the V3 hypervariable loop of HIV-1 BH10 (Neurath et al (1990), *Molec. Immunol* 27, 539–549).
Figure 10:
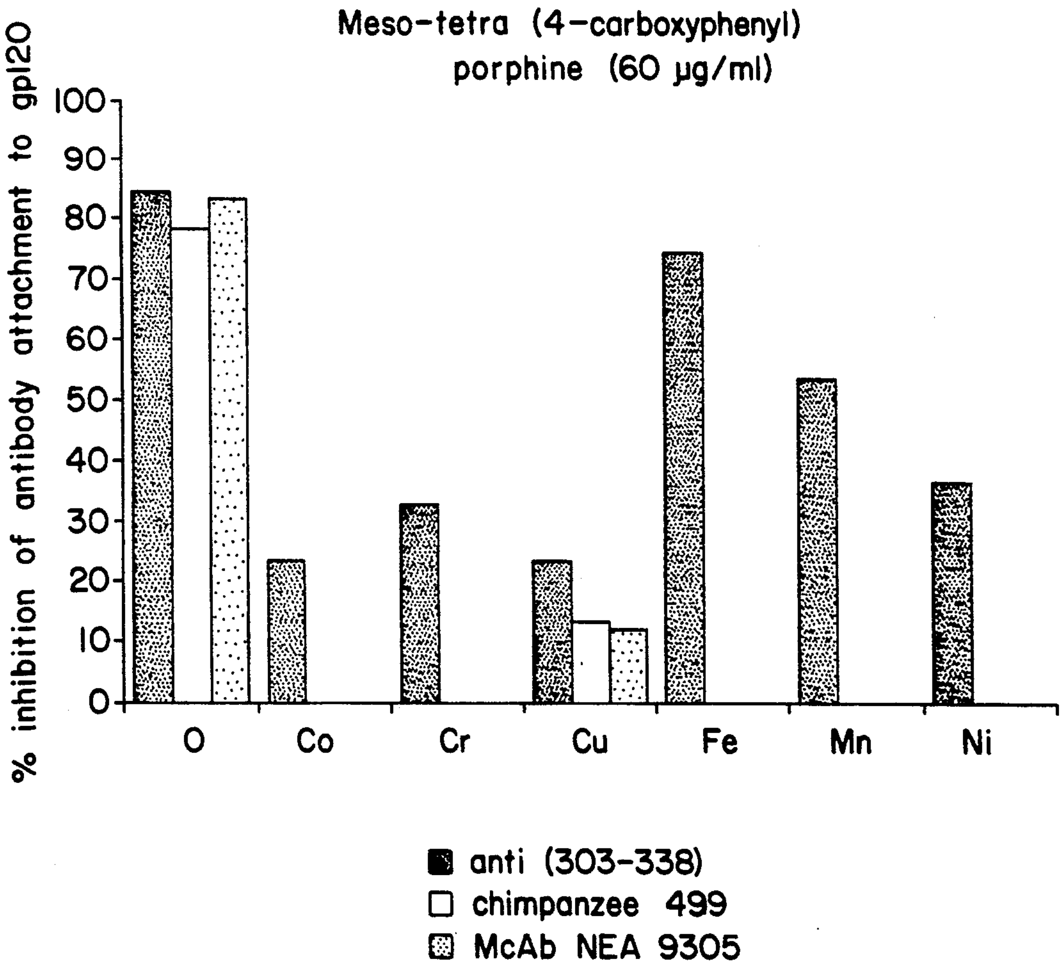
FIG. 10 is a bar graph depicting the inhibitory effect of meso-tetra (4-carboxyphenyl)porphine (60 μg/ml) and metal chelates thereof on the reaction between HIV-1 IIIB glycoprotein gp120 and three distinct antibodies reacting with the V3 hypervariable loop of this glycoprotein. The antisera used were rabbit antiserum to a synthetic peptide corresponding to the V3 hypervariable loop of HIV-1 clone BH10, serum of a chimpanzee immunized with V3 hypervariable loop peptides of distinct HIV-1 isolates and monoclonal antibodies (McAb NEA 9305) raised against a synthetic peptide corresponding to residues (315–329) of the V3 hypervariable loop of HIV-1 BH10. (Neurath et al (1990), *Molec. Immunol.*, 27, 539–549).
Figure 11:
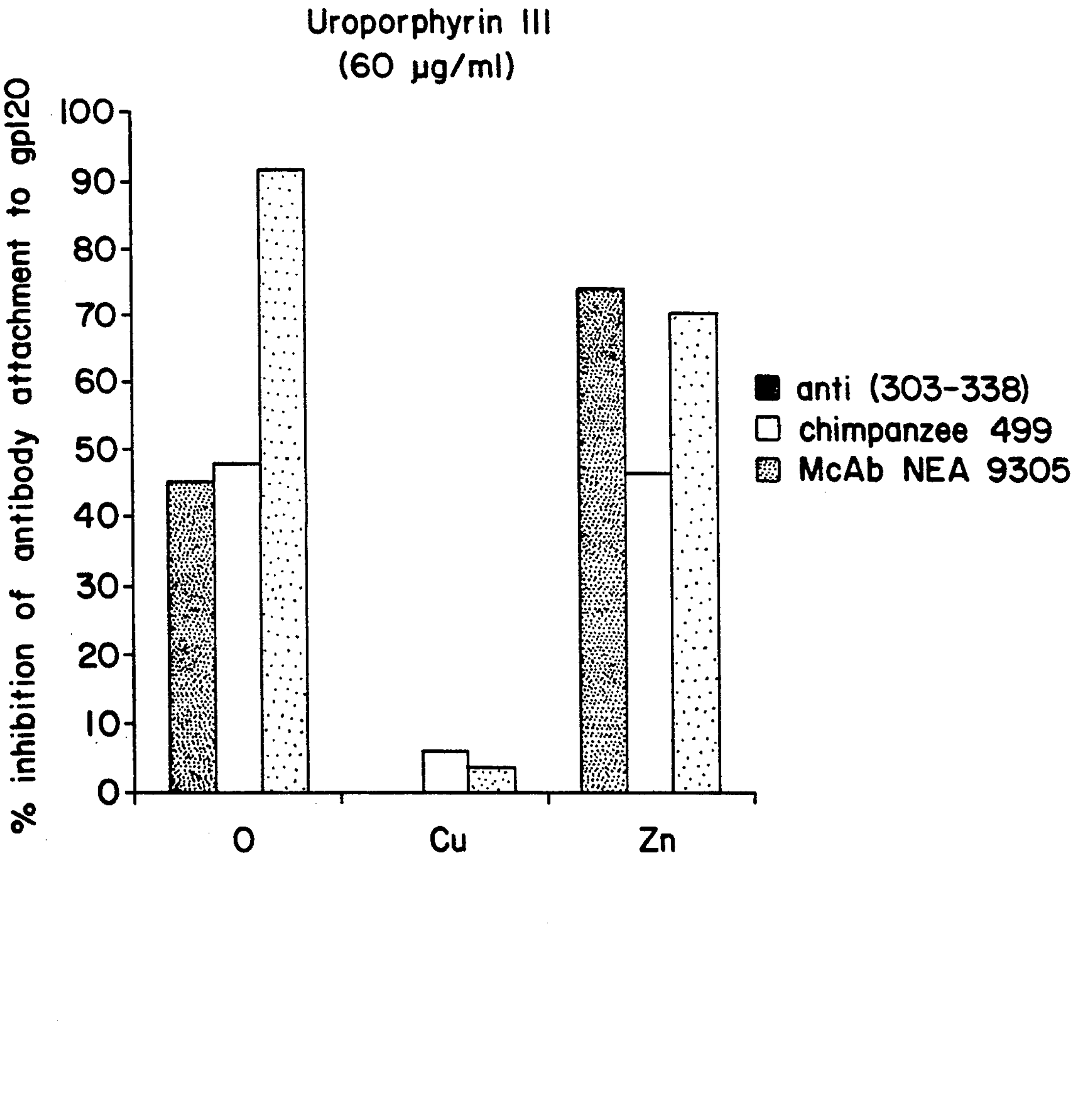
FIG. 11 is a bar graph depicting the inhibitory effect of uroporphyrin III (60 μg/ml) and metal chelates thereof on the reaction between HIV-1 IIIB glycoprotein gp120 and three distinct antibodies reacting with the V3 hypervariable loop of this glycoprotein. The antisera used were rabbit antiserum to a synthetic peptide corresponding to the V3 hypervariable loop of HIV-1 clone BH10, serum of a chimpanzee immunized with V3 hypervariable loop peptides of distinct HIV-1 isolates and monoclonal antibodies (McAb NEA 9305) raised against a synthetic peptide corresponding to residues (315-329) of the V3 hypervariable loop of HIV-1 BH10 (Neurath et al, (1990), *Molec. Immunol.*, 27, 539-549)

Since the porphyrin derivatives occur either as complexes with metals or uncomplexed, the HIV-1 inhibitory activity of porphyrin metal complexes was tested. Several porphyrin derivatives and several metals were selected for these studies. In the case of chlorin $e_6$ (substance #149 in Table 1), the uncomplexed substance and the corresponding Cu and Zn derivatives all had a considerable inhibitory activity on the interaction between the V3 hypervariable loop of HIV-1-IIIB and several antisera specific for the V3 hypervariable loop (FIG. 8). On the other hand, the inhibitory activity of the Fe derivative of deuteroporphyrin IX,2-vinyl,4-hydroxymethyl (substance #152 in Table 1) was substantially lower than that of the uncomplexed substance or of its Zn derivative (FIG. 9). In the case of mesotetra (4-carboxyphenyl) porphine (substance #160 in Table 1), all metallic derivatives tested (Co, Cr, Cu, Fe, Mn and Ni) had drastically reduced inhibitory activity in comparison with the uncomplexed substance on the reaction between the V3 hypervariable loop peptide of HIV-1-IIIB and 3 distinct antisera directed against this loop (FIG. 10). In the case of uroporphyrin III (substance #164 in Table 1), the Cu derivative had a much lower inhibitory activity in comparison with either the uncomplexed compound or its Zn derivative (FIG. 11). This indicates that the chelation of porphyrin derivatives with distinct metals may have a strong effect on their attachment to the V3 hypervariable loop of HIV-1. In particular, metallic ions occurring in several valences (Co, Cr, Cu, Fe Mn, Ni) substantially decreased the activity of porphyrin derivatives in comparison with uncomplexed porphyrins or their complexes with metallic ions predominantly existing in one form (Zn).

The effect of metalloporphyrins on the replication of HIV-1-IIIB was also assessed. The Cu and Zn derivatives of chorin $e_6$ had about 1/10th of the antiviral activity in comparison with unchelated chlorin $e_6$ ($EC_{50}$=7.1 and 8.5 μg/ml, respectively; compare with compound #149 in Table 1). Other metallic chelates of porphyrin derivatives listed in Table 1 (#152, #160, #164) had no antiviral activity. The cytotoxicity of the metallic derivatives was also dramatically increased as compared with the parent compounds (results not shown). In conclusion, the metallic derivatives of porphyrins are inferior as inhibitors of HIV-1 replication in comparison with the parent compounds free of metals.

Example 6: Testing of Porphyrin Derivatives

Figure 12A:
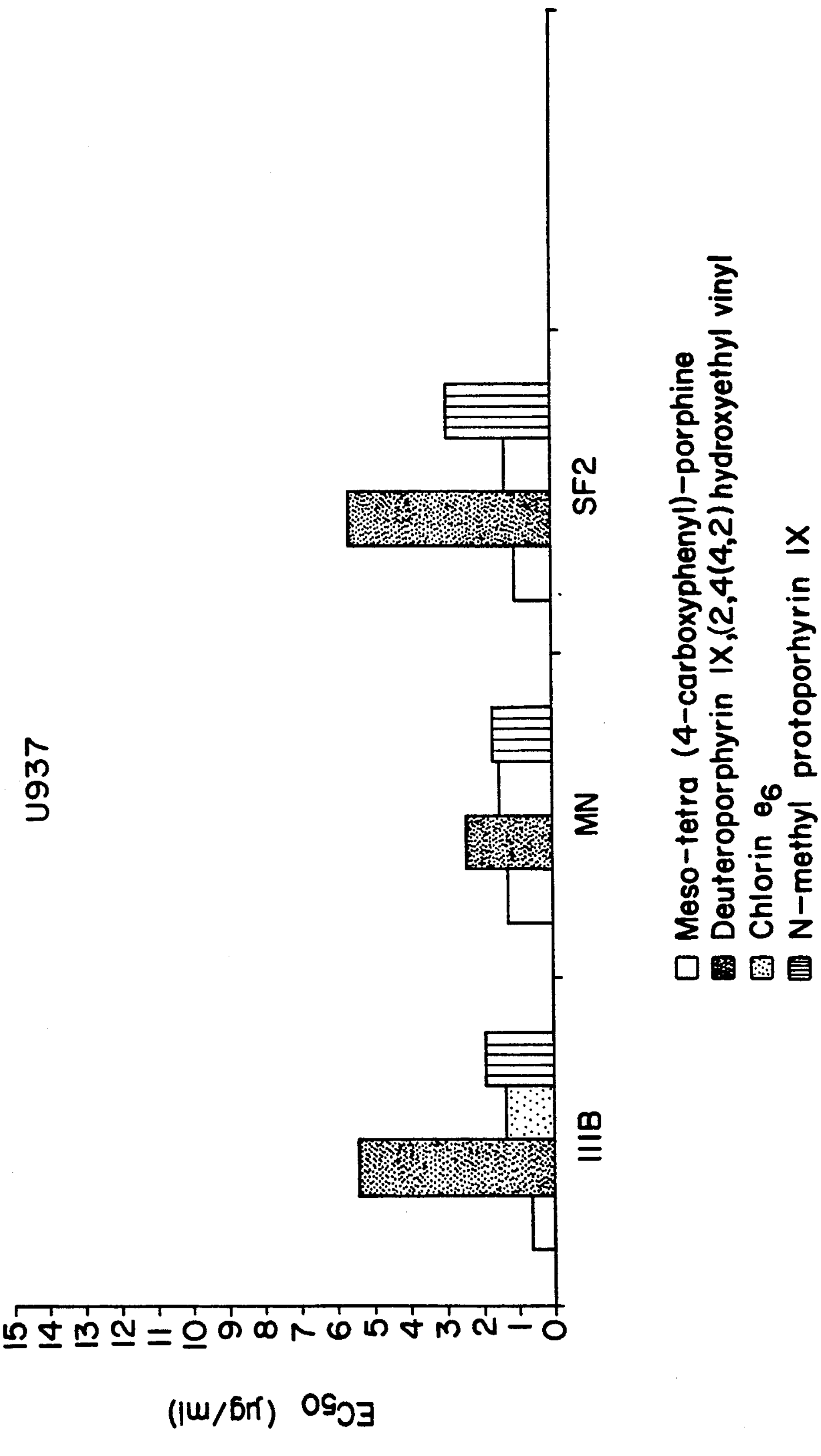
FIG. 12A and FIG. 12B are graphs depicting antiviral activity of selected porphyrin derivatives for distinct HIV-1 isolates in T-lymphocytic (MT-2) (FIG. 12B) and a promonocytic (U937) (FIG. 12A) cell lines. HIV-1 RF did not replicate in U937 cells. Therefore, the antiviral activity against HIV-1 RF could not be tested in this cell line. Note that the higher the value of $EC_{50}$, the less efficient is the drug for inhibiting HIV-1 replication.
Figure 12B:
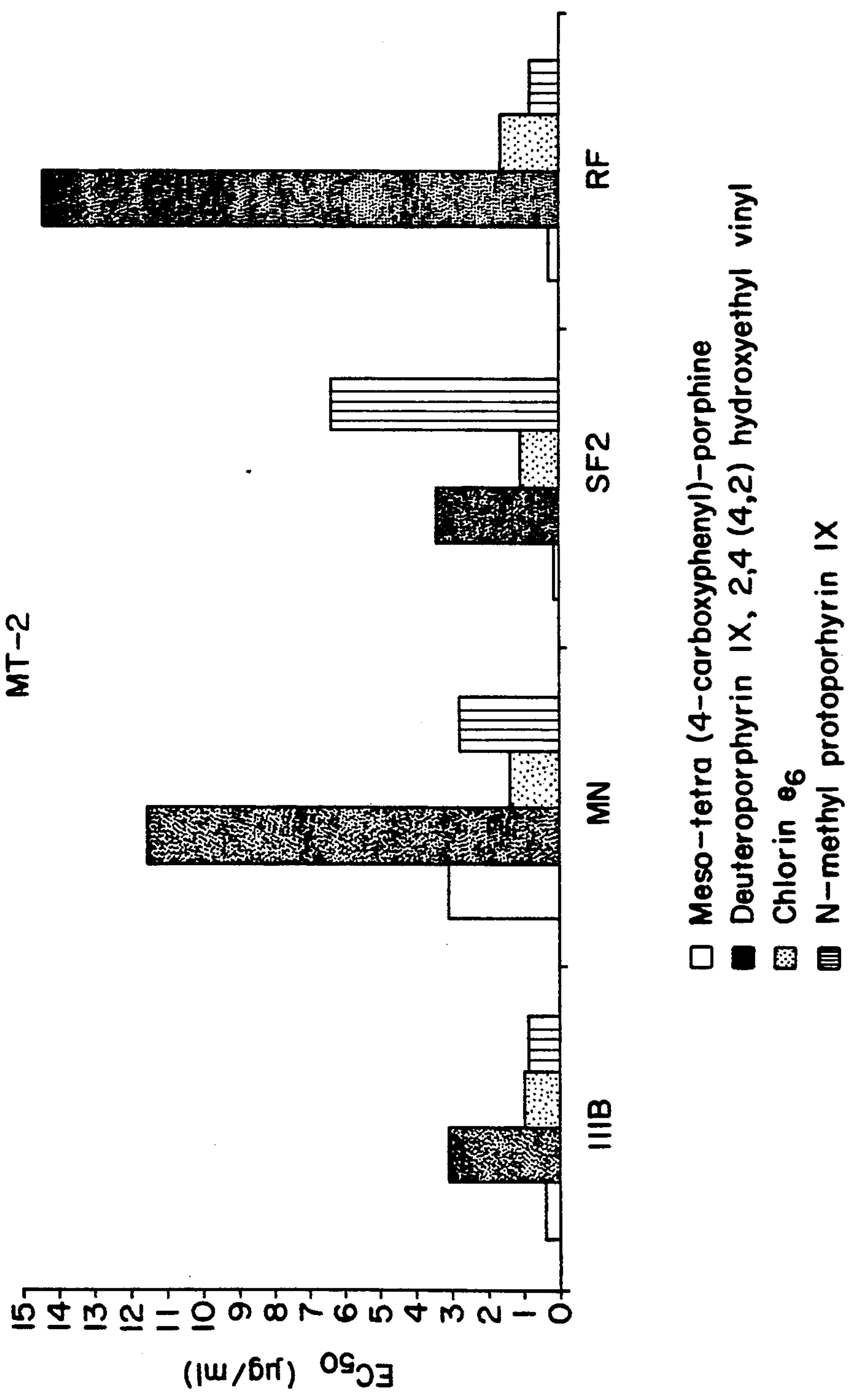

Four of the porphyrin derivatives (see FIG. 12) were tested for their inhibiting activity and the replication of four distinct HIV-1 isolates: IIIB, MN, SF2 and RF in two different cell lines, U937 and MT-2. All four derivatives inhibited virus replication in each of the two cell lines (FIG. 12) Cummulatively, the results in FIG. 12 show that meso-tetra(4-carboxyphenyl) was the most effective agent with broad specificity.

Example 7: Screening for Antiviral compounds with A Predetermined Site of Action by RIA (ELISA) Tests Data indicated that ATA in monomeric form inhibited the reaction between epitopes on the V3 hypervariable loop of gp120 and site-specific monoclonal or anti-peptide antibodies and that this inhibitory effect resulted from binding of ATA to the V3 hypervariable loop. The somewhat surprising finding that a low molecular weight substance inhibited antigen-antibody reactions suggested the possibility to screen for potential antiviral drugs by simple tests (RIA or ELISA). By selecting antibodies with predetermined specificity and/or defined segments of viral proteins for such assays, it became also possible to select antiviral drugs with already predefined modes of action.

In an initial attempt to find substances with an expected mode of action similar to that of ATA, many other chemicals were screened for inhibitory activity on gp120-antibody reactions by methods described above for ATA. Several of the substances tested had inhibitory activity, and some of these also inhibited the replication of HIV-1 in tissue culture (Table 1). The compounds with antiviral activity belonged to the categories of anions, cations, neutral substances, zwitterions (polyions) and triphenylmethane dyes (Table 1). One of the active compounds, hemin (substance #13), was reported recently to have anti-HIV-1 activity. (Levere, D. L., Gong, Y-F., Kappas, A., Bucher, D. J., Wormser, G. P., and Abraham, N. G. (1991), "Heme Inhibits Human Immunodeficiency Virus 1 Replication in Cell Cultures and Enhances the Antiviral Effect of Zidovudine," *Proc. Natl. Acad. Sci. USA*, 88, 1756–1759).

TABLE 1

CHEMICALS TESTED FOR INHIBITORY ACTIVITY ON THE REACTION BETWEEN HIV-1 gp120 AND ANTIBODIES SPECIFIC FOR THE V3 HYPERVARIABLE LOOP[b]

| | | Inhibitory activity[b] | Antiviral activity[c,d] | $EC_{50}$[d] |
|---|---|---|---|---|
| | | **Anions** | | |
| Carboxy | | | | |
| 1. | triphenylacetic acid | — | | |
| 2. | 3,3,3-triphenylpropionic acid | + (27%) | — | |
| 3. | 1,3-adamantanedicarboxylic acid | — | | |
| 4. | 4-biphenylcarboxylic acid | — | | |
| 5. | salicylic acid | — | | |
| 6. | 4,4',5,5'-azobenzenetetracarboxylic acid[z] | — | | |
| 7. | 2,2'-dihydroxy-5-5'-dicarboxyazobenzene[z] | — | | |
| 8. | alizarin yellow R[z] | — | | |
| 9. | 4-aminosalicylic acid[a] | — | | |
| 10. | 5-aminosalicylic acid[a] | — | | |
| 11. | 4-hydroxy-3(3-pyridylazo)-benzoic acid[a] | — | | |
| 12. | phenolphthalein-O,O-diacetic acid | — | | |
| 13. | hemin | (65.3%) | ⊕ (79%) | 23 μg/ml |
| Sulfonate | | | | |
| 14. | 2-anthraquinonesulfonic acid | — | | |
| 15. | 2-naphthol-6,8-disulfonic acid | — | | |
| 16. | 1,2-bis-[2-(6,8-disulfonato)-napthoxy] ethane | — | | |
| 17. | 2-(6,8-disulfonato)napthoxyethanol | — | | |
| 18. | 2-(6,8-disulfonato)napthoxyacetic acid | — | | |
| 19. | p-nitrophenyl 2-(6,8-disulfonato)-naphthoxyacetate | — | | |
| 20. | 3-amino-1,5-napthalene disulfonic acid[a] | — | | |
| 21. | 4-amino-5-hydroxy-2,7-naphthalenedisulfonic acid[a] | — | | |
| 22. | 2-naphthylamine-4,8-disulfonic acid[a] | — | | |
| 23. | 1-amino-2-naphthol-4-sulfonic acid[a] | — | | |
| 24. | 4,5-dihydroxynaphthalene-2,7-disulfonic acid | — | | |
| 25. | chromotrope 2B[z] | — | | |
| 26. | 4-aminoazobenzenesulfonic acid[z,a] | — | | |
| 27. | Congo Red[z,a] | — | | |
| 28. | Evans Blue[z,a] | — | | |
| 29. | 4-(3-hydroxy-6-methyl-2-pyridylazo) benzenesulfonic acid[z,a] | — | | |
| Other | | | | |
| 30. | sodium tetraphenylborate | — | | |
| 31. | phenolphthalein diphosphate | — | | |
| 32. | phenolphthalein carbinol disulfate | — | | |
| | | **Cations** | | |
| Ammonium | | | | |
| 33. | cyclooctylamine | — | | |
| 34. | cyclododecylamine | — | | |
| 35. | cyclen | — | | |
| 36. | 1-adamantanamine | — | | |
| 37. | 2-adamantanamine | — | | |
| 38. | 1,3-adamantanediamine | — | | |
| 39. | tritylamine | — | | |
| 40. | N-γ-trityl-glutamine | — | | |
| 41. | cyproheptadine | — | | |
| 42. | N-phenylbenzylamine | + (28.8%) | — | |
| 43. | 2,4,5-triphenylimidazole | — | | |
| 44. | 2,3,5-triphenyl-2H-tetrazolium chloride | — | | |
| 45. | qu..ine | — | | |
| 46. | 2,4,6-triphenyl1,3,5-triazine | — | | |
| Quaternary ammonium | | | | |
| 47. | 10-chloro-9-anthraldehyde trimethylammonioacetylhydrazone | — | | |
| 48. | anthrone trimethylammonioacetylhydrazone | — | | |
| 49. | fluorone black trimethylammonioacetylhydrazone | — | | |
| | | **Neutrals** | | |
| Amines | | | | |
| 50. | 2-aminobiphenyl | + (70.5%) | — | |
| 51. | 4-aminobiphenyl | — | | |
| 52. | 2-benzylaniline | — | | |
| 53. | 2,4,6-triphenylaniline | — | | |
| 54. | 4-aminobenzophenone | — | | |
| 55. | diphenylamine | — | | |

TABLE 1-continued

CHEMICALS TESTED FOR INHIBITORY ACTIVITY ON THE REACTION BETWEEN HIV-1 gp120 AND ANTIBODIES SPECIFIC FOR THE V3 HYPERVARIABLE LOOP[b]

| | Inhibitory activity[b] | Antiviral activity[c,d] | $EC_{50}$[d] |
|---|---|---|---|
| 56. benzidine | — | | |
| 57. N-phenyl-1-naphthylamine | — | | |
| 58. 1-aminoanthracene | — | | |
| 59. 1-aminoanthraquinone | — | | |
| 60. 2-aminoanthraquinone | — | | |
| 61. 9-aminophenanthren | — | | |
| 62. 2-aminofluorene | — | | |
| 63. 2-amino-7-bromofluorene | + (37.1%) | + (19%) | 68 μg/ml[d] |
| 64. 1-amino-7-nitrofluorene | — | | |
| 65. 3-aminofluoranthene | + (27.4%) | ⊕ (100%) | 3 μg/ml |
| 66. 2-aminochrysene | — | | |
| 67. 2,3-cyclododecenopyridine | + (36.8%) | + (53%) | 37 μg/ml |
| 68. acridine | — | | |
| 69. aminopyrine | — | | |
| 70. 2-aminobenzothiazole | — | | |
| 71. 2-amino-4-(4-biphenylyl)thiazole | — | | |
| 72. N[4-(4-aminobenzyl)phenyl]-5-norbornene-2,3-dicarboximide | — | | |
| 73. 4-benzeneazodiphenylamine[z] | — | | |
| 74. 2-amino-5,4'-dimethylazobenzene[z] | — | | |
| Phenols | | | |
| 75. 1-phenylphenol | — | | |
| 76. 4-phenylphenol | — | | |
| 77. p,p'-biphenol | — | | |
| 78. 4-hydroxydiphenylmethane | — | | |
| 79. 2-hydroxyfluorene | — | | |
| 80. 9-hydroxyfluorene | — | | |
| 81. quinalizarin | — | | |
| 82. tannic acid | — | | |
| 83. saligenin | — | | |
| 84. 5-methylsaligenin | — | | |
| 85. 3,5-diiodosaligenin | — | | |
| 86. salicylaldoxime | — | | |
| 87. salicylanilide | — | | |
| 88. 9-phenyl-2,3,7-trihydroxy-6-fluorene | — | | |
| 89. 4,4'-dihydroxydiphenylsulfone | — | | |
| Other neutrals | | | |
| 90. 4-bromobiphenyl | — | | |
| 91. 2-flurobiphenyl | — | | |
| 92. 4-phenylanisole | — | | |
| 93. 4-biphenylcarboxaldehyde | + (21%) | + (32%) | >80 μg/ml |
| 94. 10-chloro-9-anthraldehyde | — | | |
| 95. anthrone | — | | |
| 96. 5-(2-adamantylidene)2,2'-dimethyl-1,3-dioxane-4,6-dione | — | | |
| 97. phenyl salicylate | — | | |
| 98. 3-chloroacetamidofluoranthene | — | | |
| 99. 2-chloroacetamido-7-bromofluorene | — | | |
| 100. 4-biphenylcarbonitrile | — | | |
| 101. carbamazepine | — | | |
| 102. 4-nitrobiphenyl | — | | |
| 103. 4,4'-dinitrobiphenyl | — | | |
| 104. indigo | — | | |
| 105. triphenylphosphate | — | | |
| 106. dibenzobicyclo[2,2,2]octane-2,3-dicarboxylic acid anhydride | + (77.5%) | ⊕ (82%) | 18 μg/ml |
| 107. 2,2,3,3-tetracyanodibenzo-bicyclo[2,2,2]octane | — | | |
| Zwitterions and polyions | | | |
| 108. N-tritylglycine | + (33.5%) | — | |
| 109. N-trityl-1-phenylalanine | — | | |
| 110. N-trityl-D-phenylalanine | — | | |
| 111. 3-(2,4,5)-trihydroxyphenylalanine | — | | |
| 112. N-β-trityl-asparagine | — | | |
| 113. S-trityl-1-cysteine | — | | |
| 114. N-trityl-1-leucyl-1-alanyl-1-leucine | + (62.1%) | + (14%) | >80 μg/ml |
| 115. calcein | — | | |
| 116. actinomycin D | — | | |
| 117. aminomethanesulfonic acid | — | | |
| 118. 2-phenyliodoniobenzoate | — | | |
| 119. triphenylphosphine oxide | — | | |
| 120. triphenylphosphine sulfide | — | | |
| 121. triphenylphosphonium cyclopentadienylide | — | | |
| Triphenylmethane Dyes | | | |

TABLE 1-continued

CHEMICALS TESTED FOR INHIBITORY ACTIVITY ON THE REACTION BETWEEN HIV-1 gp120 AND ANTIBODIES SPECIFIC FOR THE V3 HYPERVARIABLE LOOP[b]

| | | Inhibitory activity[b] | Antiviral activity[c,d] | $EC_{50}$[d] |
|---|---|---|---|---|
| Phenolic,carboxylate | | | | |
| 122. | aurintricarboxylic acid | + (50%) | ⊕ (83%) | 12 μg/ml |
| 123. | phenolphthalein | — | | |
| 124. | thymolphthalein | — | | |
| 125. | fluorescein | — | | |
| 126. | eosin y | — | | |
| 127. | erythrosyn B | — | | |
| 128. | 9-phenyl-2,3,7-trihydroxy-6-fluorone | + (58.6%) | ⊕ (85%) | 27 μg/ml |
| 129. | 9-phenyl-6-fluorone-2,3, 7-tris oxyacetic acid | + (56.8%) | ⊕ (88%) | 15 μg/ml |
| 130. | 3-[bis(-3-carboxy-4-hydroxy-2-methyl-5-tert.butyl)methylene]--6-oxo-2-methyl-5-tert.butyl-1,4-cyclohexadiene-1-carboxylic acid | + (38.6%) | + (38%) | 80 μg/ml |
| 131. | 6-[bis(-3-carboxy-2-hydroxy-5-iodo)methylene]--5-oxo-2-iodo-1,3-cyclohexadiene-4-carboxylic acid | + (74.8%) | + (41%) | 71 μg/ml |
| 132. | naphthochrome green | — | | |
| Phenolic,sulfonate | | | | |
| 133. | phenol red | — | | |
| 134. | cresol red | — | | |
| 135. | thymol blue | — | | |
| 136. | bromothymol blue | — | | |
| 137. | bromcresol purple | — | | |
| Phenolic,carboxylate & sulfonate | | | | |
| 138. | chrome azurol S | — | | |
| 139. | chromoxane cyanine R | — | | |
| Phenolic,neutral | | | | |
| 140. | 6-[bis(-3-acetyl-4-hydroxy) methylene]-6-oxo-1-acetyl-1,4-cyclohexadiene | + (69.4%) | — | |
| Aniline | | | | |
| 141. | methyl violet | — | | |
| 142. | crystal violet | — | | |
| 143. | malachite green | — | | |
| Aniline,carboxy | | | | |
| 144. | rhodamine B | — | | |
| Aniline,sulfonate | | | | |
| 145. | acid fuchsin | — | | |
| | Porphyrin Derivatives | | | |
| 146. | aluminum phthalocyanine tetrasulfonate | — | | |
| 147. | coproporphyrin I dihydrochloride | — | | |
| 148. | coproporphyrin III dihydrochloride | — | | |
| 149. | chlorine $e_6$ | + (76.3%) | 100% | 0.8 μg/ml |
| 150. | deuteroporphyrin IX, 2,4 bis glycol | + (43.3%) | 99% | 38.2 μg/ml |
| 151. | deuteroporphyrin IX, 2,4 (4,2) hydroxy-ethyl vinyl | + (83.7%) | 100% | 1.9 μg/ml |
| 152. | deuteroporphyrin IX 2-vinyl 4-hydroxy-methyl | + (82.6%) | 100% | 3.0 μg/ml |
| 153. | heptacarboxylporphyrin I dihydrochloride | — | | |
| 154. | hexacarboxylporphyrin I dihydrochloride | + (40.3%) | 96% | 16.9 μg/ml |
| 155. | pentacarboxylporphyrin I dihydrochloride | — | | |
| 156. | mesobilirubin | — | | |
| 157. | N-methyl protoporphyrin IX | + (77.2%) | 100% | 0.6 μg/ml |
| 158. | protoporphyrin IX | + (55.8%) | 100% | 1.0 μg/ml |
| 159. | rhodotorulic acid | — | | |
| 160. | meso-tetra (4-carboxyphenyl) porphine | + (84.3%) | 100% | 1.3 μg/ml |
| 161. | meso-tetra (4-pyridyl) porphine | + (66.4%) | 0% | >80 μg/ml |
| 162. | meso-tetra (N-methyl-4-pyridyl)-porphine tetra tosylate | — | | |
| 163. | uroporphyrin I dihydrochloride | + (41.1%) | 99% | 9.8 μg/ml |
| 164. | uroporphyrin III dihydrochloride | + (45.0%) | 100% | 2.3 μg/ml |
| 165. | chlorophyll a | + (46.0%) | 12% | >80 μg/ml |
| 166. | chlorophyll b | + (63.4%) | 14% | >80 μg/ml |
| 167. | chlorophyllin | + (73.7%) | 14% | 64.5 μg/ml |
| 168. | vitamin B12 (cyanocobalamin) | — | | |

Legend for Table 1

[a]amine

[b]Chemicals with inhibitory activity are indicated by + with the percentage of inhibition at a 50 μg/ml concentration given in parentheses.

[c]Chemicals with inhibitory activity in ELISA (RIA) tests were tested for antiviral activity. Those with activity are indicated by +; those suppressing P24 production by ≧98% are indicated by ⊕. The percentage of inhibition of P24 nucleoprotein production by the chemicals at a final concentration of 40 μg/ml is given in parentheses.

[d]$EC_{50}$ = concentration at which the production of P24 was reduced to 50% of that detected in control cultures.

[z]azo compound

Porphyrin compounds, such as those described above, are set forth in *Porphyrin Products,* Porphyrin Products, Inc., P.O. Box 31, 195 South West, Loga, Utah 84321.

It will be appreciated that the instant specification is set forth by way of illustration and not limitation, and that various modifications and changes may be made without departure from the spirit and scope of the present invention.

What is claimed is:

1. A method for the rapid screening of a drug targeted to the V3 hypervariable loop of the human immunodeficiency virus type 1 envelope glycoprotein gp120 or the $V_3$ hypervariable loop of the human immunodeficiency virus type 2 envelop glycoprotein gp120 comprising (i) providing gp120 immobilized on a solid substrate or V3 hypervariable loop synthetic peptides immobilized on a solid substrate, (ii) providing a drug for targeting to said V3 hypervariable loop and (iii) measuring the inhibitory effect of the drug on the interaction between (a) said gp120 immobilized on a solid substrate or said V3 hypervariable loop synthetic peptides immobilized on a solid substrate and (b) antibodies specific for the V3 hypervariable loop of HIV-1 gp 120 or the V3 hypervariable loop of HIV-2 gp120.

2. The method of claim 1, wherein the antibodies are polyclonal antibodies.

3. The method of claim 1, wherein the antibodies are monoclonal antibodies.

4. The method of claim 1, wherein the synthetic peptide consists essentially of the amino acid sequence of the V3 hypervariable loop of HIV-1 gp 120 or HIV-2 gp 120.

5. A method for the rapid screening of a drug targeted to the V3 hypervariable loop of the human immunodeficiency virus type 1 or type 2 envelope glycoprotein gp 120 which comprises (a) incubating (i) a first antibody, said first antibody capable of binding to the V3 hypervariable loop of HIV-1 gp 120 or HIV-2 gp 120, (ii) a drug to be screened, and (iii) an antigen selected from the group consisting of gp 120 immobilized on a solid substrate and V3 hypervariable loop synthetic peptides of HIV-1 gp 120 or HIV-2 gp 120, immobilized on a solid substrate, (b) washing and removing excess unbound first antibody, (c) detecting the bound antibody of the V3 hypervariable loop of HIV-1 gp120 or HIV-2 gp 120 by (i) adding a labeled second antibody, said second antibody being capable of binding with the first antibody, (ii) washing and removing excess unbound second antibody, (iii) determining the amount of the label, (d) repeating steps (a) to (c) in the absence of the drug, and (e) determining the inhibitory effect of the drug, in percentages, by the following formula:

$$\frac{\text{(quantity of the label in the absence of the drug)} - \text{(quantity of the label in the presence of the drug)}}{\text{quantity of the label in the absence of the drug}} \times 100.$$

6. A method for the rapid screening of a drug targeted to the V3 hypervariable loop of the human immunodeficiency virus type 1 or type 2 envelope glycoprotein gp 120 which comprises (a) incubating (ii) a drug to be screened, (iii) an antigen selected from the group consisting of gp 120 immobilized on a solid substrate and V3 hypervariable loop synthetic peptides of HIV-1 gp 120 or HIV-2 gp 120, immobilized on a solid substrate, (b) washing and removing excess unbound labeled antibody, (c) determining the amount of the label, (d) repeating steps (a) to (c) in the absence of the drug and (e) determining the inhibitory effect of the drug, in percentages, by the following formula:

$$\frac{\text{(quantity of the label in the absence of the drug)} - \text{(quantity of the label in the presence of the drug)}}{\text{quantity of the label in the absence of the drug}} \times 100.$$

7. A method for the rapid screening of a drug targeted to the V3 hypervariable loop of the human immunodeficiency virus type 1 or type 2 envelope glycoprotein gp 120 which comprises (a) incubating (i) an antibody, said antibody capable of binding to the V3 hypervariable loop of HIV-1 gp 120 or HIV-2 gp 120, (ii) a drug to be screened, and (iii) a labeled antigen, said antigen selected from the group consisting of gp 120 immobilized on a solid substrate and V3 hypervariable loop synthetic peptides of HIV-1 gp 120 or HIV-2 gp 120, immobilized on a solid substrate, (b) washing and removing excess unbound labeled antigen, (c) determining the amount of the label, (d) repeating steps (a) to (c) in the absence of the drug and (e) determining the inhibitory effect of the drug, in percentages, by the following formula:

$$\frac{\text{(quantity of the label in the absence of the drug)} - \text{(quantity of the label in the presence of the drug)}}{\text{quantity of the label in the absence of the drug}} \times 100.$$

* * * * *